(12) United States Patent
Shimoyama

(10) Patent No.: US 12,383,119 B2
(45) Date of Patent: *Aug. 12, 2025

(54) BALLOON FOR ULTRASONIC ENDOSCOPE

(71) Applicant: FUJIFILM Corporation, Tokyo (JP)

(72) Inventor: Yuto Shimoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 253 days.

This patent is subject to a terminal disclaimer.

(21) Appl. No.: 17/902,901

(22) Filed: Sep. 5, 2022

(65) Prior Publication Data

US 2023/0108503 A1 Apr. 6, 2023

(30) Foreign Application Priority Data

Sep. 27, 2021 (JP) .................................. 2021-156431

(51) Int. Cl.
  *A61B 1/00* (2006.01)
  *A61B 8/00* (2006.01)

(52) U.S. Cl.
  CPC .......... *A61B 1/00082* (2013.01); *A61B 8/445* (2013.01); *A61B 8/4483* (2013.01); *A61B 8/4281* (2013.01)

(58) Field of Classification Search
  CPC .............................. A61B 8/12; A61B 1/00082
  See application file for complete search history.

(56) References Cited

U.S. PATENT DOCUMENTS

| 8,758,251 B2 | 6/2014 | Kohno | |
| 2011/0251458 A1 * | 10/2011 | Terliuc | ............... A61B 1/00082 600/116 |

(Continued)

FOREIGN PATENT DOCUMENTS

| JP | S53107190 | 9/1978 |
| JP | S5690210 | 7/1981 |

(Continued)

OTHER PUBLICATIONS

"Office Action of Co-pending, U.S. Appl. No. 17/902,903", issued on May 22, 2024, p. 1-p. 17.

(Continued)

*Primary Examiner* — Joseph M Santos Rodriguez
*Assistant Examiner* — Tommy T Ly
(74) *Attorney, Agent, or Firm* — JCIPRNET

(57) ABSTRACT

Provided is a balloon for an ultrasonic endoscope in which an ultrasound oscillator surface of an ultrasound transducer can be most swollen.

A balloon for an ultrasonic endoscope that is mounted to cover an outside surface of an ultrasound transducer provided in a distal end part body on a distal end side of an insertion part includes a bottomed tubular balloon body that has an opening portion provided at one end in a first direction corresponding to a longitudinal direction of the insertion part and attached to the distal end part body, covers an oscillator surface of the ultrasound transducer, and stores an ultrasonic wave transmission medium inside, to be swellable, and a swelling restricting part that, in a case where the ultrasonic wave transmission medium is stored inside the balloon body, makes an oscillator surface region facing the oscillator surface of the ultrasound transducer most swollen by restricting a part of the balloon body.

8 Claims, 15 Drawing Sheets

(56) References Cited

U.S. PATENT DOCUMENTS

| | | | |
|---|---|---|---|
| 2013/0218018 A1 | 8/2013 | Kurihara | |
| 2013/0331814 A1 | 12/2013 | Fulton, III et al. | |
| 2015/0173709 A1 | 6/2015 | Whitmore, III | |
| 2015/0250465 A1 | 9/2015 | Kaiser et al. | |
| 2016/0249859 A1* | 9/2016 | Babkin | A61B 8/445 |
| | | | 600/509 |
| 2017/0157368 A1 | 6/2017 | Umeda et al. | |
| 2019/0142246 A1 | 5/2019 | Horrisberger et al. | |
| 2020/0046216 A1 | 2/2020 | Moein | |
| 2020/0323419 A1 | 10/2020 | Okada et al. | |
| 2021/0386429 A1 | 12/2021 | Franano et al. | |
| 2021/0393334 A1* | 12/2021 | Wilson | A61B 17/320725 |
| 2024/0206708 A1 | 6/2024 | Okada et al. | |

FOREIGN PATENT DOCUMENTS

| | | | |
|---|---|---|---|
| JP | S618036 | | 1/1986 |
| JP | S62186701 | | 11/1987 |
| JP | H04244144 | | 9/1992 |
| JP | H0819542 | | 1/1996 |
| JP | H08131442 | | 5/1996 |
| JP | H08322843 | | 12/1996 |
| JP | 2003169804 | | 6/2003 |
| JP | 2004254942 | | 9/2004 |
| JP | 2019500116 | | 1/2019 |
| JP | 2019068931 | | 5/2019 |
| JP | 2019068931 A | * | 5/2019 |
| JP | 2020171435 | | 10/2020 |
| WO | 2018231857 | | 12/2018 |

OTHER PUBLICATIONS

"Office Action of co-pending U.S. Appl. No. 17/902,903", issued on Sep. 10, 2024, pp. 1-18.

"Office Action of Related, U.S. Appl. No. 17/902,903", issued on Dec. 19, 2024, p. 1-p. 6.

"Office Action of Related U.S. Appl. No. 17/902,904", issued on Jan. 17, 2025, p. 1-p. 33.

"Office Action of U.S. Related Application, U.S. Appl. No. 17/902,903", issued on Feb. 26, 2025, p. 1-p. 18.

"Notice of Reasons for Refusal of Japan Related Application, Application No. 2021-156429", issued on Jan. 6, 2025, with English translation thereof, p. 1-p. 8.

"Notice of Reasons for Refusal of Japan Related Application, Application No. 2021-156430", issued on Jan. 6, 2025, with English translation thereof, p. 1-p. 8.

"Notice of Reasons for Refusal of Japan Counterpart Application", issued on Dec. 26, 2024, with English translation thereof, p. 1-p. 6.

"Decision of Refusal of Japan Counterpart Application", issued on Mar. 5, 2025, with English translation thereof, p. 1-p. 6.

"Office Action of U.S. Related Application, U.S. Appl. No. 17/902,904", issued on Apr. 30, 2025, p. 1-p. 28.

"Office Action of Japan Counterpart Application", issued on Mar. 28, 2025, with English translation thereof, p. 1-p. 8.

"Office Action of U.S. Related Application, U.S. Appl. No. 17/902,903", issued on Jun. 17, 2025, p. 1-p. 24.

* cited by examiner

FIG. 8
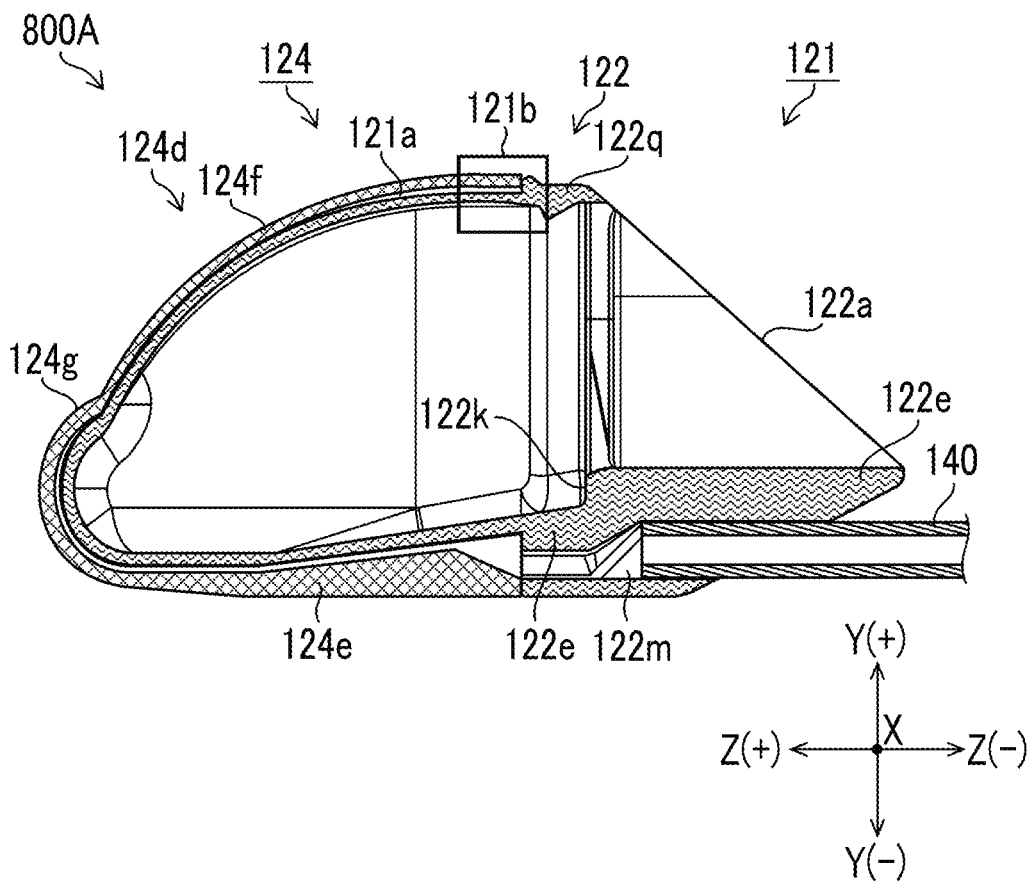
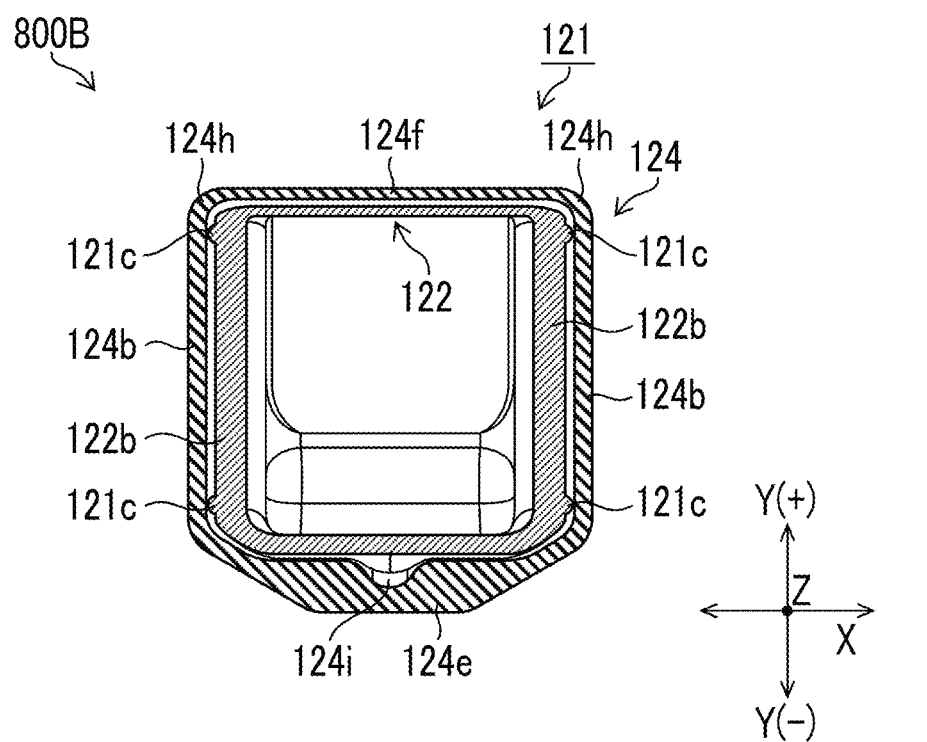

FIG. 9
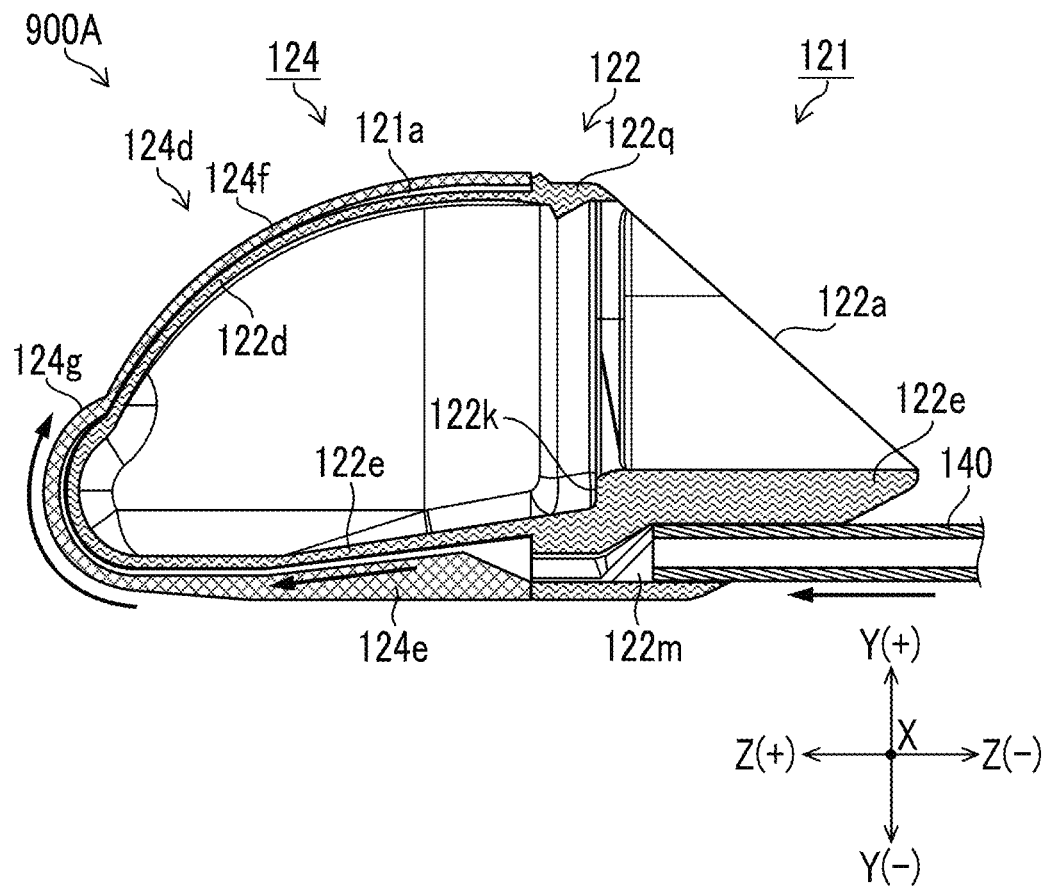
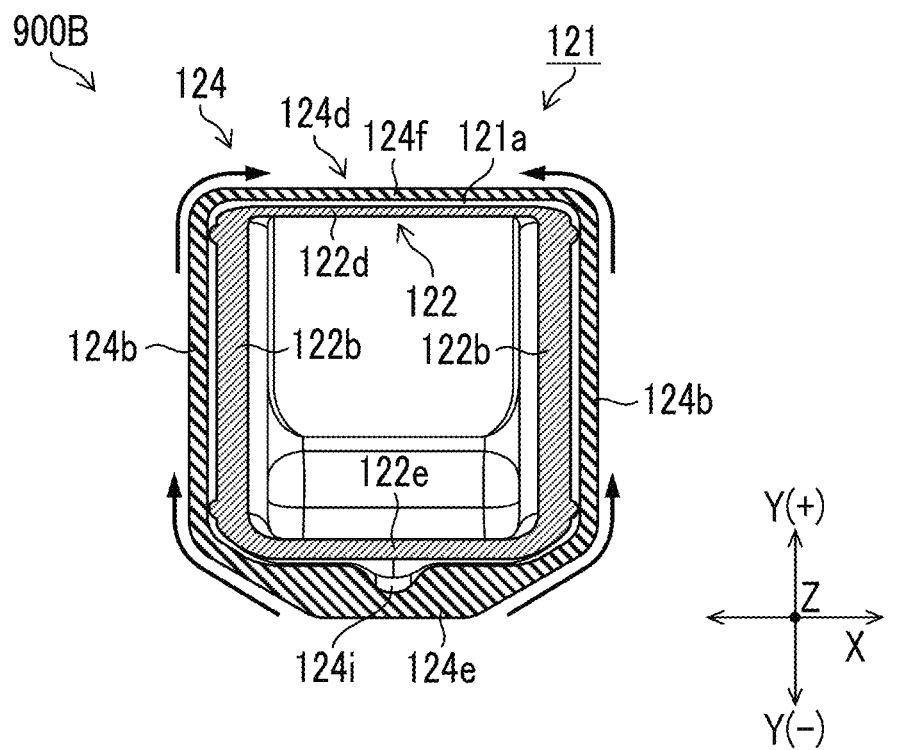

FIG. 10
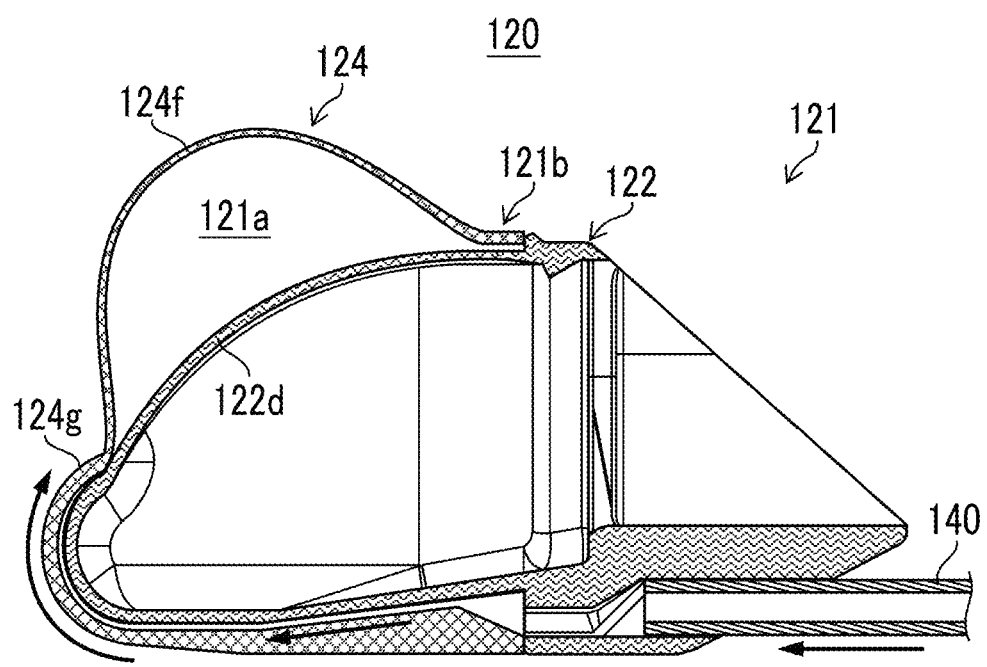
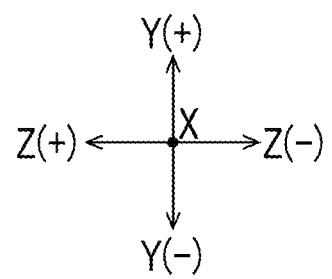

FIG. 14
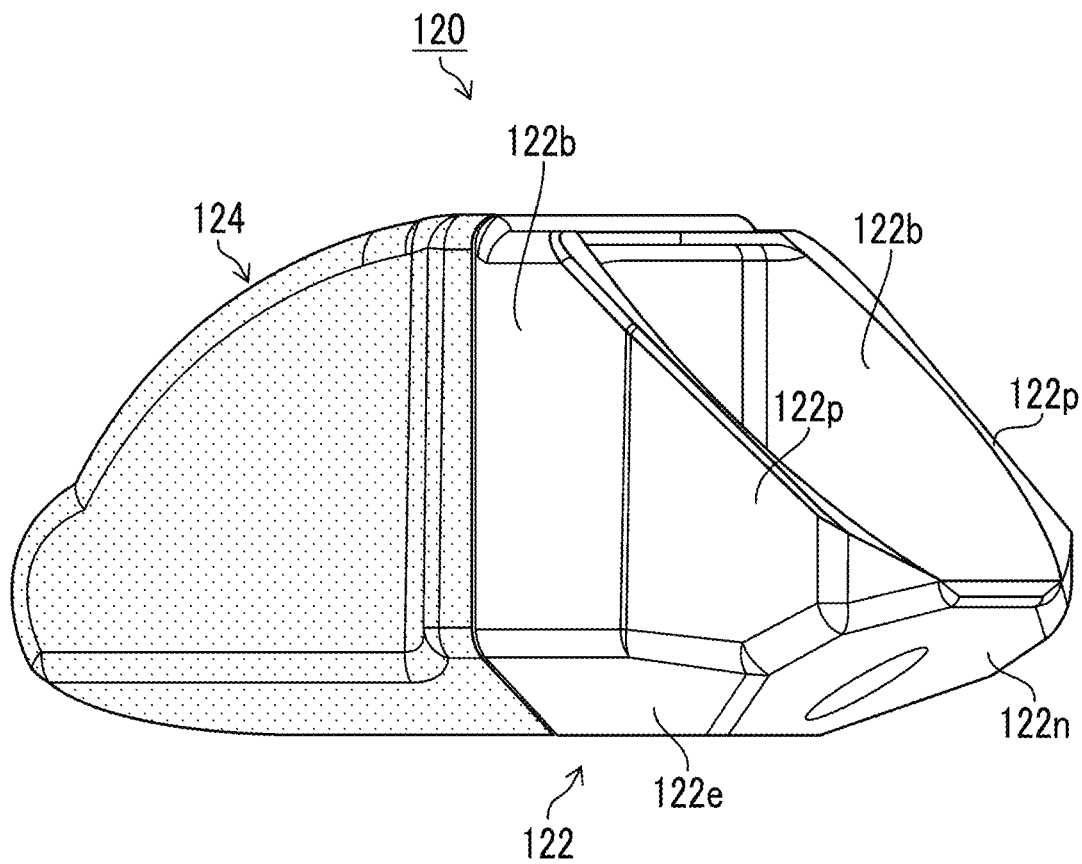
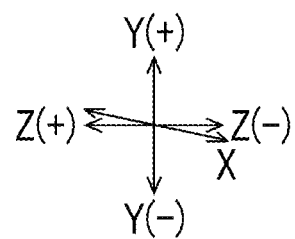

BALLOON FOR ULTRASONIC ENDOSCOPE

CROSS-REFERENCE TO RELATED APPLICATION

The present application claims priority under 35 U.S.C § 119(a) to Japanese Patent Application No. 2021-156431 filed on Sep. 27, 2021, which is hereby expressly incorporated by reference, in its entirety, into the present application.

BACKGROUND OF THE INVENTION

1. Field of the Invention

The present invention relates to a balloon for an ultrasonic endoscope, and in particular, to a balloon that is mounted on a distal end part of an insertion part of an ultrasonic endoscope.

2. Description of the Related Art

In the medical field, an ultrasonic endoscope is used. The ultrasonic endoscope is an endoscope that disposes an imaging element and an ultrasound transducer integrally in a distal end part of an insertion part that is inserted into a body cavity of a subject. The ultrasound transducer emits an ultrasonic wave toward a site to be observed in the body cavity and receives an echo signal reflected from the site to be observed, and an electric signal depending on the received echo signal is output to an ultrasonic observation device. Then, the electric signal is subjected to various kinds of signal processing in the ultrasonic observation device, and is then displayed as an ultrasound tomographic image on a monitor or the like.

The ultrasonic wave and the echo signal are considerably attenuated in the air. For this reason, there is a need to interpose an ultrasonic wave transmission medium, such as water or oil, between the ultrasound transducer and the site to be observed. Accordingly, an expandable balloon is mounted on a distal end part of an ultrasonic endoscope, and the ultrasonic wave transmission medium is injected into the balloon to expand the balloon to be brought into contact with the site to be observed. As a result, air is eliminated from a region between the ultrasound transducer and the site to be observed, and the attenuation of the ultrasonic wave and of the echo signal is restrained.

Various balloons that are mounted on the distal end part of the insertion part of the ultrasonic endoscope have been suggested.

JP2004-254942A discloses a technique in which a groove that surrounds an oscillator is provided at an insertion part distal end, and a balloon is mounted in the groove. JP1996-131442A (JP-H08-131442A) discloses a technique in which a restricting unit that restricts expansion of a balloon in a scanning axis direction on an ultrasound transducer is provided. JP1978-107190A (JP-S53-107190A) discloses an ultrasound diagnostic apparatus having a flexible film body attached to a probe body to form a sealed space in front of an ultrasonic wave transmission and reception surface, and a fluid with which the sealed space is filled.

SUMMARY OF THE INVENTION

In a case where the balloon is mounted at a position covering an outside surface of the ultrasound transducer, for example, in diagnosis or treatment of a narrow path, such as a bronchus in a body cavity, by an ultrasonic bronchial endoscope, in a case where a balloon including a distal end part in which the ultrasound transducer is disposed is swollen in a spherical shape, an outer diameter of the balloon increases, and a contact position of an oscillator surface may not be stable.

The present invention has been accomplished in view of such a situation, and an object of the present invention is to provide a balloon for an ultrasonic endoscope in which an ultrasound oscillator surface of an ultrasound transducer can be most swollen.

A first aspect of the present invention provides a balloon for an ultrasonic endoscope that is mounted to cover an outside surface of an ultrasound transducer provided in a distal end part body on a distal end side of an insertion part, the balloon comprising a bottomed tubular balloon body that has an opening portion provided at one end in a first direction corresponding to a longitudinal direction of the insertion part and attached to the distal end part body, covers an oscillator surface of the ultrasound transducer, and stores an ultrasonic wave transmission medium inside, to be swellable, and a swelling restricting part that, in a case where the ultrasonic wave transmission medium is stored inside the balloon body, makes an oscillator surface region facing the oscillator surface of the ultrasound transducer most swollen by restricting a part of the balloon body.

A second aspect of the present invention is the balloon for an ultrasonic endoscope, in which the balloon body has at least a two-layer structure including an inner part that has the opening portion at one end and an outer part that covers the inner part and that is bonded on an opening portion side, a storage portion that stores the ultrasonic wave transmission medium is provided between the inner part and the outer part, and the outer part has an oscillator surface region.

A third aspect of the present invention is the balloon for an ultrasonic endoscope, in which an adhesion portion for bonding the inner part and the outer part is provided, and the adhesion portion functions as the swelling restricting part.

A fourth aspect of the present invention is the balloon for an ultrasonic endoscope, in which the outer part includes a thick portion that is formed to have a thickness greater than a thickness of the oscillator surface region, on the other end side opposite to the one end in the first direction, and the thick portion functions as the swelling restricting part.

A fifth aspect of the present invention is the balloon for an ultrasonic endoscope, in which the outer part includes thick portions that are formed to have a thickness greater than a thickness of the oscillator surface region, on both sides in a second direction perpendicular to the first direction of the oscillator surface region, and transition portions that are formed between the thick portions and the oscillator surface region, and the transition portions function as the swelling restricting part.

A sixth aspect of the present invention is the balloon for an ultrasonic endoscope, in which adhesion regions of the inner part and of the outer part are provided on both sides in a second direction perpendicular to the first direction of the oscillator surface region, and the adhesion regions function as the swelling restricting part.

A seventh aspect of the present invention is the balloon for an ultrasonic endoscope, in which the balloon body has a region smaller than a distance between standing wall portions provided on both sides of the ultrasound transducer before the distal end part body is mounted.

An eighth aspect of the present invention is the balloon for an ultrasonic endoscope, in which the balloon body includes a protrusion portion that protrudes to a distal end part body side and that is fitted into a groove portion of the distal end part body formed on a proximal end side of the ultrasound transducer.

A ninth aspect of the present invention is the balloon for an ultrasonic endoscope, in which the balloon body includes a locking portion that is locked to a stepped portion formed on a surface of the distal end part body on an opposite side of the ultrasound transducer.

With the balloon for an ultrasonic endoscope of the present invention, the ultrasound oscillator surface of the ultrasound transducer can be most swollen.

BRIEF DESCRIPTION OF THE DRAWINGS

FIG. 8 is a sectional view of the balloon for an ultrasonic endoscope.

FIG. 9 is a sectional view illustrating a flow of an ultrasonic wave transmission medium that is supplied to the balloon for an ultrasonic endoscope.

FIG. 10 is a sectional view showing a state in which an oscillator surface region of the balloon for an ultrasonic endoscope is swollen.

FIG. 14 is a perspective view as the balloon for an ultrasonic endoscope with the tube omitted is viewed from a proximal end side.

DESCRIPTION OF THE PREFERRED EMBODIMENTS

Hereinafter, an ultrasonic endoscope on which a balloon for an ultrasonic endoscope according to the present invention is mounted will be described with reference to the accompanying drawings.

Overall Configuration of Ultrasonic Endoscope

Figure 1:
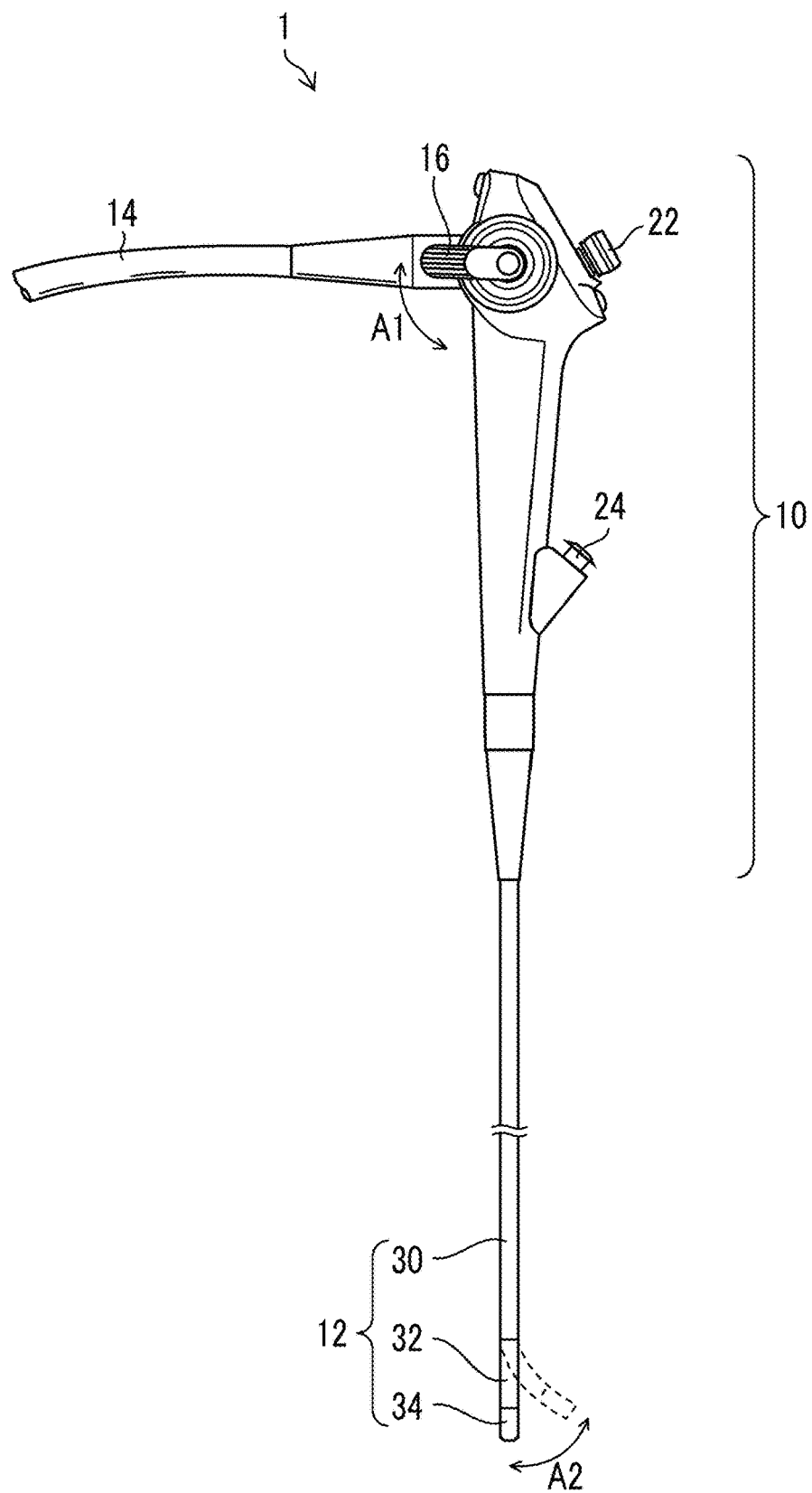
FIG. 1 is a general view of an ultrasonic endoscope (endoscope).

FIG. 1 is a general view of the ultrasonic endoscope 1. As shown in FIG. 1, the ultrasonic endoscope 1 (hereinafter, simply referred to as an "endoscope 1") is used for collection or the like of a cellular tissue of a lesion part (an observation part, a test part, or an examination part can be used). In the present embodiment, description will be provided in connection with a lymph node as an example of a lesion part.

The endoscope 1 is configured with an operating part 10 that is gripped by a practitioner and that is used for various operations, an insertion part 12 that is inserted into a body of a patient, and a universal cord 14. The endoscope 1 is connected to system constituent devices that configure an endoscope system, such as a processor device, a light source device, and an ultrasonic observation device (not shown), through the universal cord 14.

The operating part 10 is provided with various operation members that are operated by the practitioner. For example, an angle lever 16, a suction button 22, and the like are provided.

The operating part 10 is provided with a treatment tool inlet port 24 through which a treatment tool is inserted into a treatment tool insertion channel 23 (see FIG. 3) that is inserted into the insertion part 12.

The insertion part 12 extends from a distal end of the operating part 10 and is formed in a small-diameter elongated shape as a whole. The insertion part 12 is configured with, in order from a proximal end side toward a distal end side, a soft part 30, a bendable part 32, and a distal end part body 34 as a distal end part.

The soft part 30 occupies most of the insertion part 12 from the proximal end side and has enough flexibility to be bent in any direction. In a case where the insertion part 12 is inserted into a body cavity, the soft part 30 is bent along an insertion path into the body cavity.

The bendable part 32 is bent in an up-down direction (A2 direction) by rotating the angle lever 16 of the operating part 10 in an A1 direction. With the bending operation of the bendable part 32, the distal end part body 34 can be directed in a desired direction.

Though details will be described with reference to FIGS. 2 and 3 described below, the distal end part body 34 comprises an observation optical system 40 and illumination optical systems 44 that are provided to capture an observation image in a body, an ultrasound transducer 50 that acquires an ultrasound image, and a treatment tool outlet port 52 (hereinafter, referred to as an outlet port 52) from which the treatment tool inserted from the treatment tool inlet port 24 is led out.

The universal cord 14 includes a signal cable 54, a signal cable 56, and light guides 58 shown in FIG. 3 described below in detail. A connector is provided in an end portion (not shown) of the universal cord 14. The connector is connected to predetermined system constituent devices that configure the endoscope system, such as a processor device, a light source device, and an ultrasonic observation device. As a result, power, control signals, illumination light, and the like necessary for the operation of the endoscope 1 are supplied from the system constituent devices to the endoscope 1. A signal of the observation image acquired by the observation optical system 40 and a signal of the ultrasound image acquired by the ultrasound transducer 50 are transmitted from the endoscope 1 to the system constituent devices. The signals transmitted to the system constituent devices are subjected to image processing, the observation image and the ultrasound image are displayed on a monitor, and the practitioner or the like can observe the images.

The configuration of the operating part 10 is not limited to the aspect shown in FIG. 1. A pair of angle knobs may be provided instead of the angle lever 16, and the bendable part 32 may be bent in the up-down direction and in a right-left direction by rotating a pair of angle knobs. An air/water supply button may be provided in the operating part 10, and gas, such as air, a liquid for cleaning, or the like may be supplied to the distal end part body 34 by operating the air/water supply button.

Configuration of Distal End Part Body

Figure 2:
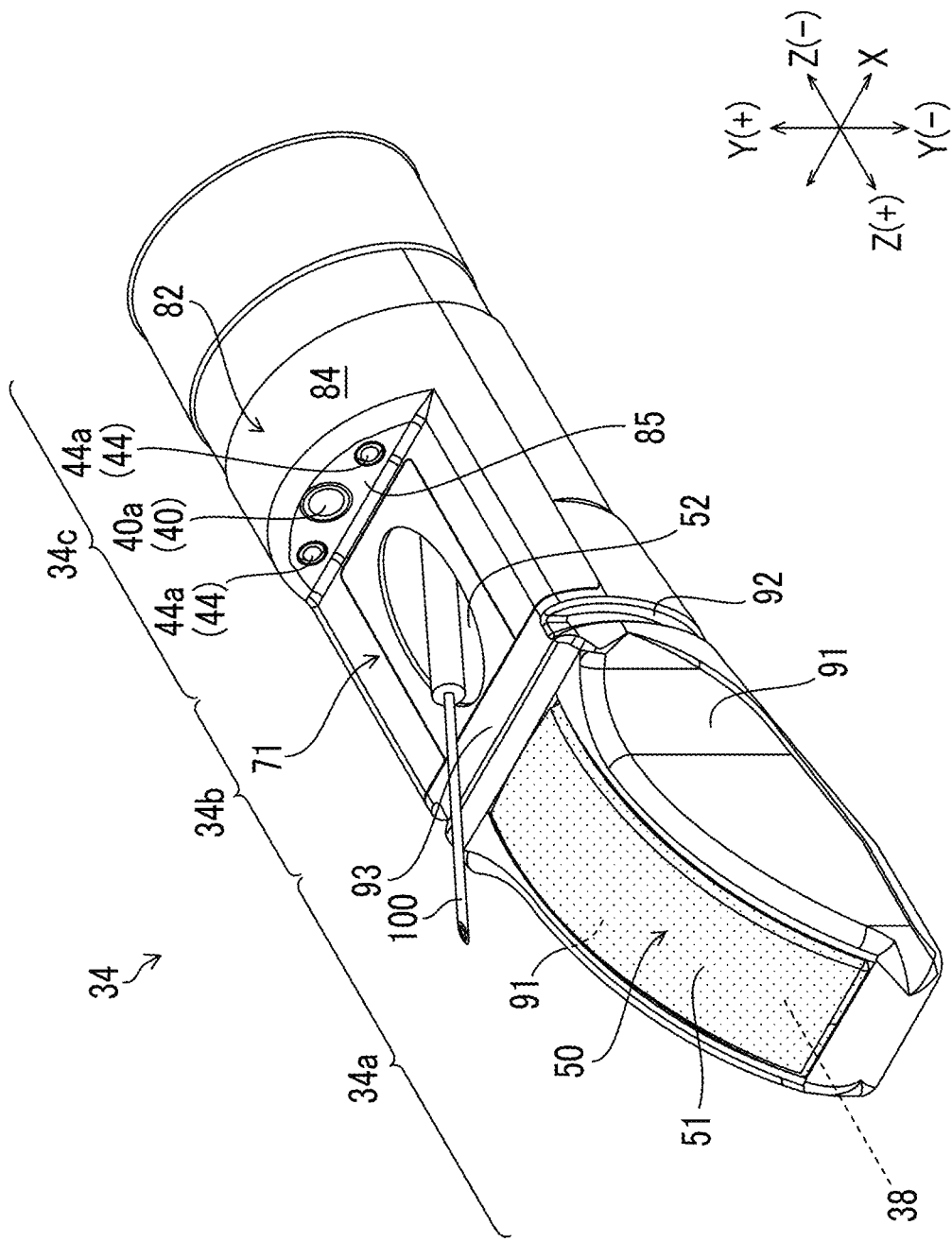
FIG. 2 is a perspective view of a distal end part body.

FIG. 2 is a perspective view of the distal end part body 34 from which a puncture needle is led out. FIG. 3 is a sectional view of the distal end part body 34.

Hereinafter, in describing the configuration of each part, a three-dimensional rectangular coordinate system of an X axis, a Y axis, and a Z axis is used. A Z direction in the drawings is a direction parallel to a longitudinal axis 38 of the distal end part body 34 (insertion part 12). A Z(+) direction side of the Z direction in the drawings is a distal end side of the distal end part body 34, and a Z(−) direction side is a proximal end side of the distal end part body 34. The Z direction in the drawings corresponds to a first direction of the present invention. A Y direction in the drawings is perpendicular to the Z direction and is an up-down direction in each drawing in the present embodiment. A Y(+) direction side as one direction side of the Y direction is an up direction, and a Y(−) direction side as the other direction side opposite to the one direction side of the Y direction is a down direction. An X direction in the drawings is a direction perpendicular to both the Z direction and the Y direction and corresponds to a second direction of the present invention.

Figure 3:
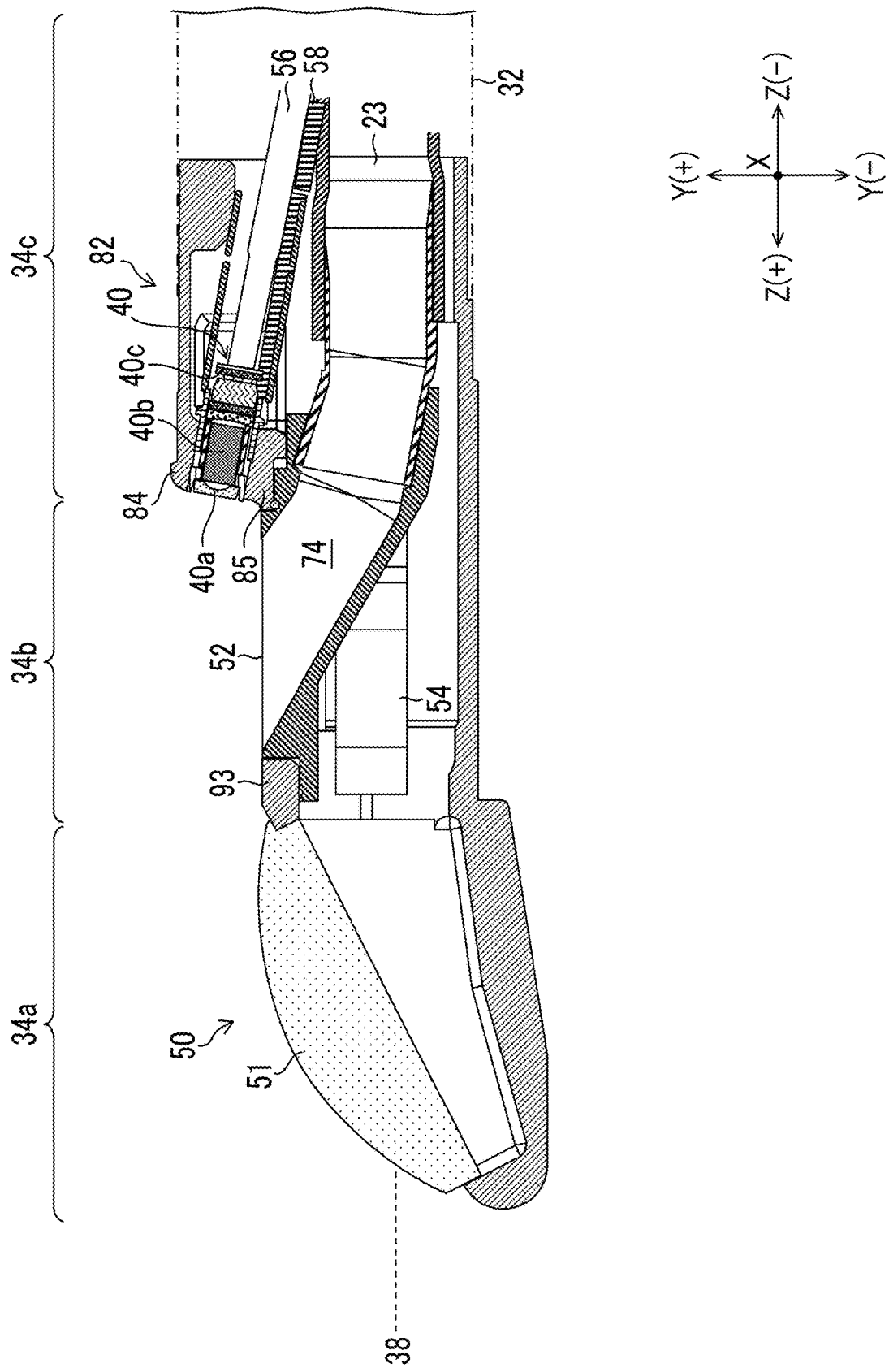
FIG. 3 is a sectional view of the distal end part body.

As shown in FIGS. 2 and 3, the distal end part body 34 comprises, from the distal end side toward the proximal end side of the distal end part body 34, an ultrasonic attachment part 34a, an outlet port forming portion 34b, and a body part 34c (see FIGS. 2 and 3).

The ultrasound transducer 50 is attached to the ultrasonic attachment part 34a in a posture tilted forward (inclined) to the Y(−) direction side with respect to the longitudinal axis 38 in a case where the distal end part body 34 is viewed from the X direction side. The ultrasound transducer 50 is a convex type that has an oscillator surface 51 on which ultrasound oscillators that transmit and receive ultrasonic waves are arranged in an arc shape along a direction of the longitudinal axis 38 (first direction). The ultrasound transducer 50 transmits ultrasonic waves from the oscillator surface 51 toward a living body and receives an ultrasound echo reflected by a living body tissue on the oscillator surface 51. A signal that generates an ultrasound image of a lymph node is acquired by the ultrasound transducer 50. The number of ultrasound oscillators that configure the ultrasound transducer 50 is not limited.

The outlet port forming portion 34b has an outlet port 52 for a treatment tool that is opened on the Y(+) direction side, and a substantially rectangular opening forming surface 71 parallel to an XZ plane in which the outlet port 52 is opened and along the Z direction (including the longitudinal axis 38; the same applies hereinafter). The opening forming surface 71 is a surface parallel to the XZ plane and along the Z direction, and configures a part of an outer peripheral surface of the distal end part body 34. In the present embodiment, although the outlet port 52 is opened in the planar opening forming surface 71, the outlet port 52 may be opened in surfaces of various shapes, such as a curved surface, an inclined surface, or an uneven surface. In the present embodiment, description will be provided in connection with a puncture needle 100 that is used in tissue collection, such as a lymph node, as an example of the treatment tool.

A pipe line 74 is formed inside the outlet port forming portion 34b and the body part 34c. A distal end side of the pipe line 74 is connected to the outlet port 52, and a proximal end side of the pipe line 74 is connected to the treatment tool insertion channel 23 inserted into the insertion part 12. As a result, a distal end of the puncture needle 100 inserted from the treatment tool inlet port 24 is guided to the outlet port 52 by way of the treatment tool insertion channel 23 and the pipe line 74, and is led out from the outlet port 52 to the outside.

The body part 34c comprises an optical system storage portion 82 in which the observation optical system 40 and the illumination optical systems 44 are disposed. The optical system storage portion 82 has a substantially semi-cylindrical shape, and has a convex surface 84 and a stepped surface 85. The convex surface 84 configures a part of the outer peripheral surface of the distal end part body 34 (optical system storage portion 82). The convex surface 84 is positioned on the Y(+) direction side with respect to the opening forming surface 71 and has a shape along the Z direction. The convex surface 84 may be formed in various shapes, such as a curved surface, an inclined surface, or an uneven surface.

The stepped surface 85 is an inclined surface that connects a proximal end side of the opening forming surface 71 and a distal end side of the convex surface 84, and configures a part of the outer peripheral surface of the distal end part body 34. The inclined surface used herein includes a vertical surface having an inclined angle of 90° with respect to the Z direction.

The stepped surface 85 is provided with an observation window 40a of the observation optical system 40 and illumination windows 44a of a pair of illumination optical systems 44.

The observation optical system 40 includes the observation window 40a provided in the stepped surface 85, and a lens system 40b and an imaging element 40c provided in the optical system storage portion 82. The imaging element 40c is a charge coupled device (CCD) type or a complementary metal oxide semiconductor (CMOS) type image sensor and captures an observation image taken from the observation window 40a through the lens system 40b. Then, the imaging element 40c outputs an imaging signal of the observation image to the system constituent devices through the signal cable 56 inserted into the insertion part 12.

The illumination optical systems 44 are provided on both sides of the observation optical system 40 in the X direction, and each of the illumination optical systems 44 includes the illumination window 44a provided in the stepped surface 85, and the light guide 58 inserted into the insertion part 12. An emission end of the light guide 58 is disposed behind each illumination window 44a. As a result, illumination light supplied from the light source device to each light guide 58 is emitted from each illumination window 44a.

As described above, in the distal end part body 34, the ultrasound transducer 50, the outlet port 52, and the stepped surface 85 (observation window 40a) are disposed in order from the distal end side toward the proximal end side. That is, the outlet port 52 is disposed between the ultrasound transducer 50 and the observation window 40a. For this reason, a puncture place toward a lymph node in a bronchial wall surface by the puncture needle 100 can be observed with the observation optical system 40.

Ultrasonic Endoscope System

Next, an ultrasonic endoscope system of the embodiment will be described. The ultrasonic endoscope system has the above-described endoscope 1 comprising the distal end part body 34 provided on the distal end side of the insertion part 12 and the ultrasound transducer 50 provided in the distal end part body 34, and a balloon 120 for an ultrasonic endoscope (see FIG. 7, hereinafter, referred to as a "balloon") that covers an outside surface of the ultrasound transducer 50.

Figure 4:
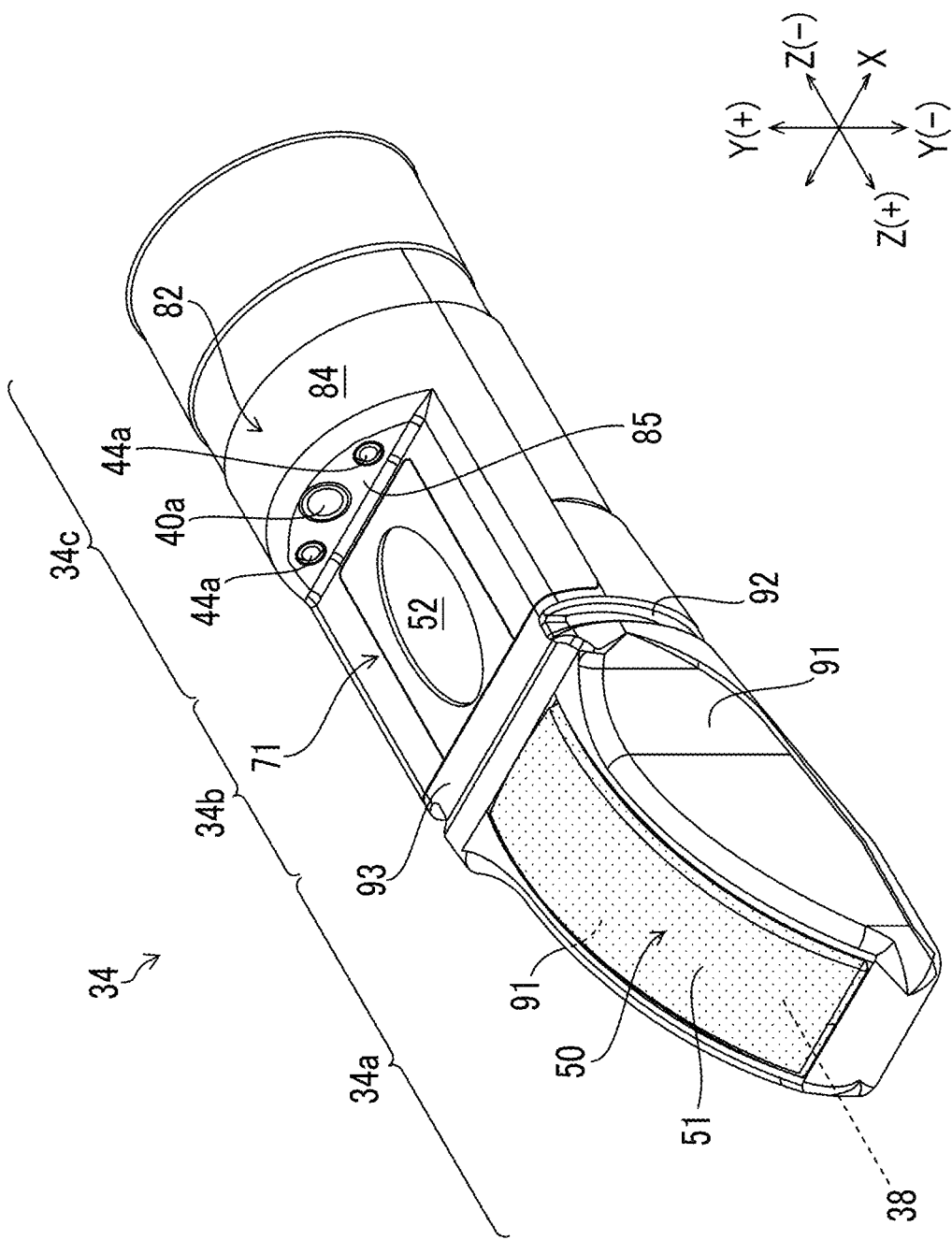
FIG. 4 is a perspective view of the distal end part body.
Figure 5:
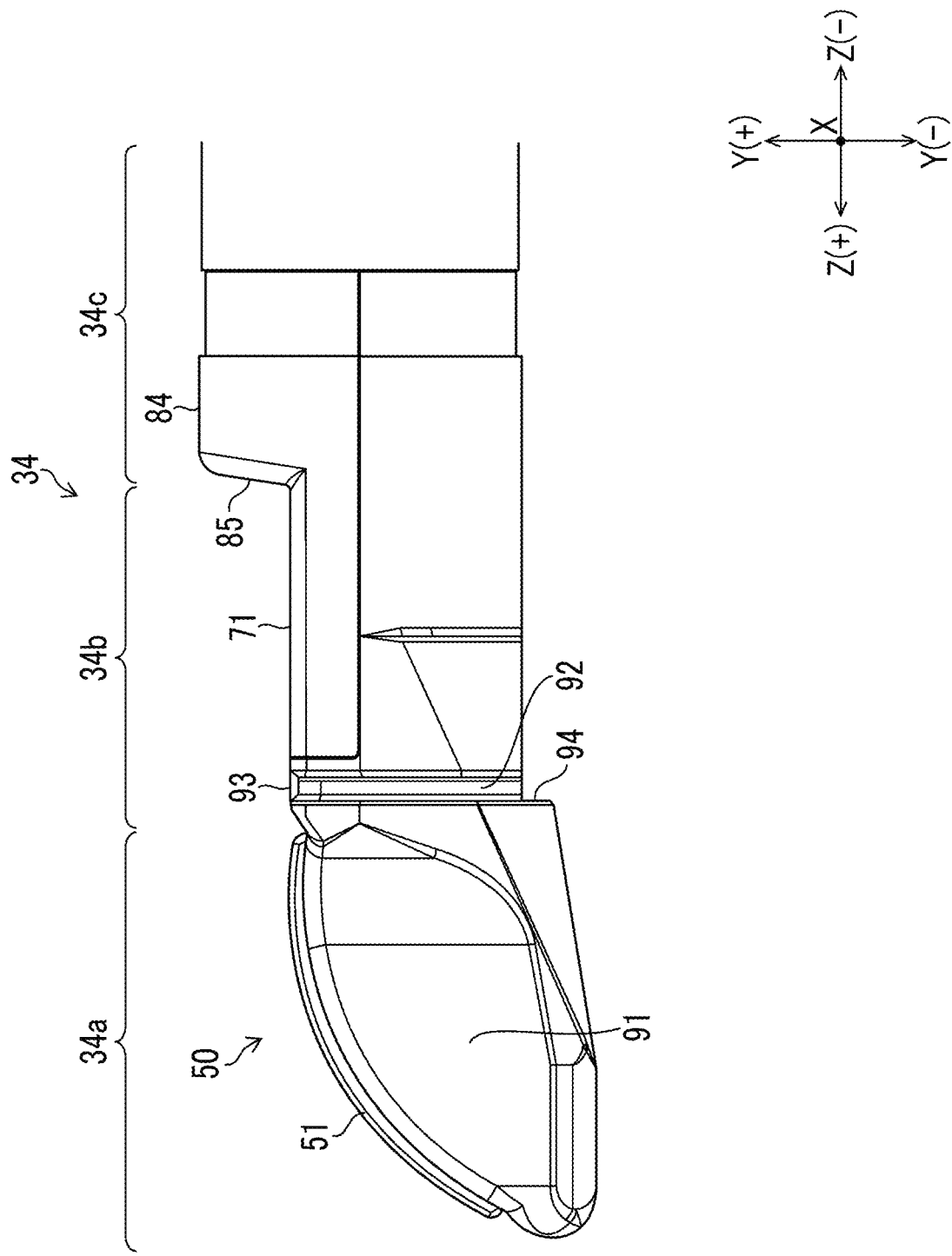
FIG. 5 is a side view of the distal end part body.
Figure 6:
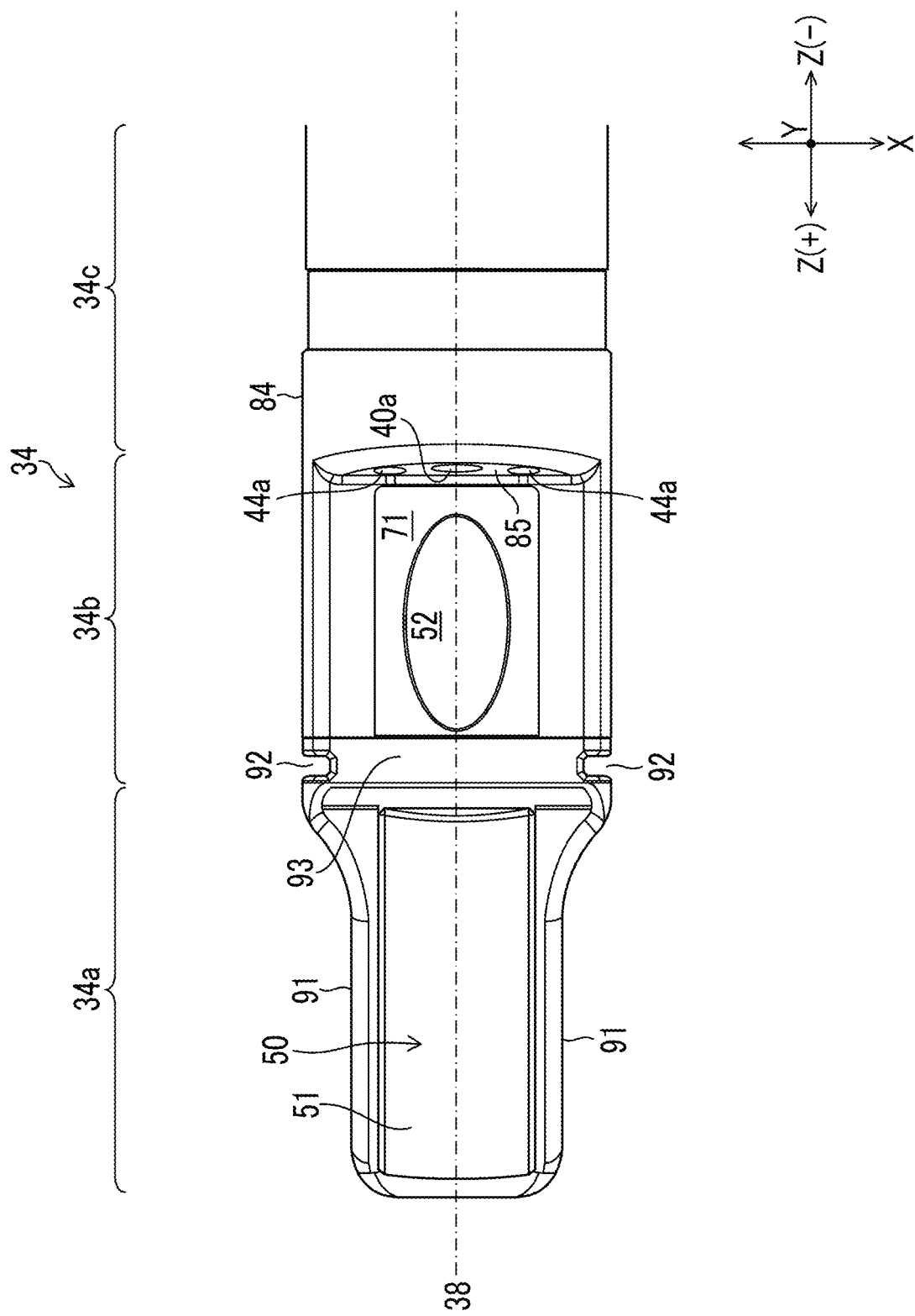
FIG. 6 is a plan view of the distal end part body.

The configuration of the distal end part body 34 on which the balloon 120 is mounted will be described. FIG. 4 is a perspective view of the distal end part body 34. FIG. 5 is a side view of the distal end part body 34. FIG. 6 is a plan view of the distal end part body 34.

The distal end part body 34 has standing wall portions 91 on both side surfaces of the ultrasound transducer 50 in a width direction (X direction) that is a direction perpendicular to the first direction (Z direction) and is a direction parallel to a plane direction of the oscillator surface 51 of the ultrasound transducer 50. The two standing wall portions 91 are configured with surfaces parallel to a YZ plane. The standing wall portions 91 do not need to be parallel to the YZ plane over the entire surface, and parallel can mean substantially parallel. A distance between the two standing wall portions 91 in the width direction, that is, a width of the ultrasonic attachment part 34*a*, is shorter than other portions (the outlet port forming portion 34*b* and the body part 34*c*) of the distal end part body 34 in a case of being viewed from the Y direction (see FIG. 6).

Fixing portions of the balloon 120 described below are in close contact with and fixed to the standing wall portions 91, whereby the balloon is fixed to the distal end part body 34.

The distal end part body 34 has a plane portion 93 between the ultrasound transducer 50 and the outlet port 52. The plane portion 93 is a plane substantially parallel to the XZ plane and has a length in the X direction longer than a length in the Z direction. The plane portion 93 is connected on the distal end side of the above-described opening forming surface 71, and the plane portion 93 and the opening forming surface 71 configure an integrated plane.

The distal end part body 34 has groove portions 92 on both side surfaces of the distal end part body 34 in the X direction between the ultrasound transducer 50 and the outlet port 52. In other words, as shown in FIG. 6, in a case where the distal end part body 34 is viewed from the Y(+) direction side, the groove portions 92 are disposed between the ultrasound transducer 50 and the outlet port 52. The groove portions 92 extend from both end portions (Y(−) direction side) of the plane portion 93 in parallel to the Y direction (see FIG. 5) and are disposed on both sides of the plane portion 93 (see FIG. 6). That is, the groove portions 92 are disposed on a proximal end side (Z(−) direction side) of the ultrasound transducer 50 and are disposed on both sides of the ultrasound transducer 50 in a case where the distal end part body 34 is viewed from the Z(+) direction side. In FIGS. 4 to 6, although the groove portions 92 are provided on the proximal end side of the ultrasound transducer 50, positions where the groove portions 92 are formed are not limited to the proximal end side of the ultrasound transducer 50, and may be provided in the standing wall portions 91.

As described below, in regard to the groove portions 92, protrusion portions 122*j* that are provided in a fixing portion of the balloon 120 are fitted into the groove portions 92. The groove portions 92 and the protrusion portions 122*j* are fitted, whereby it can be made difficult for the balloon 120 to fall off from the distal end part body 34.

The distal end part body 34 has a stepped portion 94 on a surface on an opposite side to the oscillator surface 51 on the proximal end side (Z(−) direction side) of the ultrasound transducer 50 (see FIG. 5). The stepped portion 94 is a plane substantially parallel to the XY plane and protrudes in the Y(−) direction as viewed from the Z(−) direction.

As described below, the stepped portion 94 is locked to a locking portion 122*k* that is provided in the fixing portion of the balloon 120, whereby it is possible to restrain the balloon 120 from falling off from the distal end part body 34.

Configuration of Balloon

Next, the balloon of the embodiment will be described. In the drawings, similarly to FIGS. 2 to 6, description will be provided using the three-dimensional rectangular coordinate system of the X axis, the Y axis, and the Z axis. The X axis, the Y axis, and the Z axis coincide with the X direction, the Y direction, and the Z direction in a case where the balloon 120 is mounted on the distal end part body 34. A Z(+) direction side is a distal end side, and a Z(−) direction side is a proximal end side. The Z direction in the drawings corresponds to a first direction of the present invention and corresponds to a longitudinal direction of the insertion part. A Y direction in the drawings is perpendicular to the Z direction and is an up-down direction in each drawing in the present embodiment. A Y(+) direction side as one direction side of the Y direction is an up direction, and a Y(−) direction side as the other direction side opposite to the one direction side of the Y direction is a down direction. An X direction in the drawings is a direction perpendicular to both the Z direction and the Y direction and corresponds to a second direction of the present invention.

Figure 7:
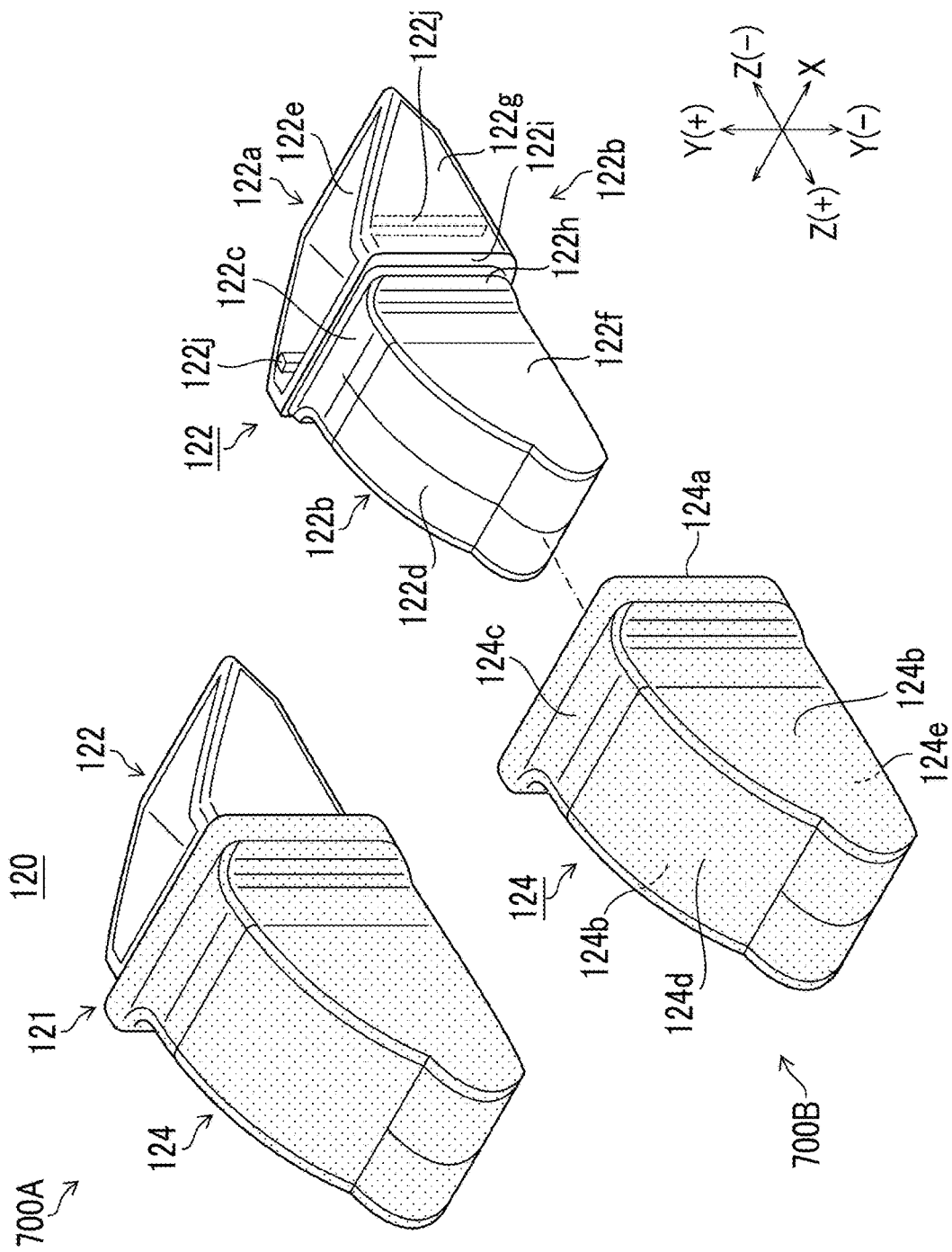
FIG. 7 is an exploded assembly diagram of a balloon for an ultrasonic endoscope in which a tube is omitted.

FIG. 7 is an assembly diagram of the balloon 120 in which a tube is omitted, 700A of FIG. 7 is a perspective view after assembly, and 700B of FIG. 7 is a perspective view before assembly. As shown in FIG. 7, the balloon 120 is configured with a balloon body 121 of a two-layer structure including an inner part 122 and an outer part 124.

Inner Part

The inner part 122 has an opening portion 122*a* at one end in the first direction (Z direction), and comprises two side surface portions 122*b* disposed to face each other, a top surface portion 122*c*, an inclined surface portion 122*d*, and a bottom surface portion 122*e*. The inner part 122 is configured in a bottomed tubular shape having the opening portion 122*a*, and portions other than the opening portion 122*a* are closed by the two side surface portions 122*b*, the top surface portion 122*c*, the inclined surface portion 122*d*, and the bottom surface portion 122*e*.

Each side of the two side surface portions 122*b*, the top surface portion 122*c*, and the bottom surface portion 122*e* that define the opening portion 122*a* is linear, and a shape of the opening portion 122*a* is a substantially rectangular shape.

The opening portion 122*a* is inclined from a downside (Y(−) side) to an upside (Y(+) side) from the proximal end side (Z(−) side) toward the distal end side (Z(+) side).

Each of the side surface portions 122*b* extends along the first direction (Z direction) and is configured with surfaces substantially parallel to the YZ plane. Each of the side surface portions 122*b* comprises a first side surface portion 122*f* that is positioned on a top surface portion 122*c* side and on an inclined surface portion 122*d* side, and a second side surface portion 122*g* that is positioned on an opening portion 122*a* side. A distance between the first side surface portions 122*f* facing each other is smaller than a distance between the second side surface portions 122*g* facing each other. A stepped portion 122*h* is formed between the first side surface portion 122*f* and the second side surface portion 122*g*.

The inner part 122 comprises a flange portion 122*i* that surrounds an outer periphery of the inner part 122. The flange portion 122*i* is provided on a proximal end side of the top surface portion 122*c* and on a proximal end side of the first side surface portion 122*f* and is also provided in the bottom surface portion 122*e* (not shown). The flange portion 122*i* is configured with four connected linear portions and is provided to surround the outer periphery of the inner part 122.

The inclined surface portion 122*d* has a shape following the oscillator surface 51 of the ultrasound transducer 50 described above and is inclined in an arc shape from an upside (Y(+) side) to a downside (Y(−) side) from the proximal end side (Z(−) side) toward the distal end side (Z(+) side).

The side surface portions 122b have the two protrusion portions 122j facing each other on inner surfaces of the second side surface portions 122g. The two protrusion portions 122j extend in parallel in the Y direction and protrude in a direction approaching each other.

Outer Part

The outer part 124 has an opening portion 124a at one end in the first direction (Z direction), and comprises two side surface portions 124b disposed to face each other, a top surface portion 124c, an inclined surface portion 124d, and a bottom surface portion 124e. The outer part 124 is configured in a bottomed tubular shape having the opening portion 124a, and portions other than the opening portion 124a are closed by the two side surface portions 124b, the top surface portion 124c, the inclined surface portion 124d, and the bottom surface portion 124e.

Each side of the two side surface portions 122b, the top surface portion 122c, and the bottom surface portion 122e that define the opening portion 124a is linear, and a shape of the opening portion 124a is a substantially rectangular shape.

Each of the side surface portions 124b extends along the first direction (Z direction) and is configured with surfaces substantially parallel to the YZ plane. The opening portion 124a of the outer part 124 is widened to a side surface portion 124b side (X direction) to house the stepped portion 122h of the inner part 122.

The inclined surface portion 124d has a shape following the oscillator surface 51 of the ultrasound transducer 50 described above and is inclined in a curved shape from the upside (Y(+) side) to the downside (Y(−) side) from the proximal end side (Z(−) side) toward the distal end side (Z(+) side).

Balloon Body

As shown in 700A, the inner part 122 is housed in the outer part 124 through the opening portion 124a of the outer part 124, and the outer part 124 covers the inner part 122. Note that the outer part 124 does not need to cover the entire inner part 122. The outer part 124 covers the two first side surface portions 122f, the top surface portion 122c, the inclined surface portion 122d, and a part (distal end side) of the bottom surface portion 122e of the inner part 122. On the other hand, the outer part 124 does not cover the second side surface portions 122g and a part (proximal end side) of the bottom surface portion 122e of the inner part 122.

As shown in 700A, the two side surface portions 122b and the two side surface portions 124b that configure the inner part 122 and the outer part 124 are disposed to face each other, respectively, the top surface portion 122c and the top surface portion 124c are disposed to face each other, the inclined surface portion 122d and the inclined surface portion 124d are disposed to face each other, and the bottom surface portion 122e and the bottom surface portion 124e are disposed to face each other.

A peripheral edge portion of the opening portion 124a of the outer part 124 comes into contact with the flange portion 122i of the inner part 122. With the flange portion 122i, a relative position of the outer part 124 with respect to the inner part 122 is determined.

The outer part 124 is bonded on the opening portion 122a side of the inner part 122, and the balloon body 121 having the two-layer structure is configured. The balloon body 121 is configured in a bottomed tubular shape that has the opening portion 122a provided at one end in the first direction (Z direction) of the insertion part 12 and attached to the distal end part body 34.

As a material for the balloon body 121, to make a configuration in which it is difficult for the inner part 122 and the outer part 124 to stick to each other, it is preferable that the inner part 122 and the outer part 124 are formed of different materials. Note that, as described below, a clearance is provided between the inner part 122 and the outer part 124, whereby it is possible to restrain the inner part 122 and the outer part 124 from being stuck to each other. Accordingly, the inner part 122 and the outer part 124 may be formed of the same material. As the materials for the inner part 122 and the outer part 124, silicon rubber, natural rubber, or the like can be used.

In a case where the balloon 120 is mounted on the distal end part body 34, the first side surface portions 122f of the inner part 122 and the standing wall portions 91 are disposed to face each other, and the inclined surface portion 122d and the ultrasound transducer 50 are disposed to face each other. The side surface portions 124b of the outer part 124 and the standing wall portions 91 are disposed to face each other with the first side surface portions 122f interposed therebetween, and the inclined surface portion 124d and the ultrasound transducer 50 are disposed to face each other with the inclined surface portion 122d interposed therebetween.

The opening portion 122a provided in the inner part 122 is an insertion port into which the above-described distal end part body 34 is inserted. An internal space of the inner part 122 is a similar shape to the shape of the distal end part body 34, and is formed in a shape smaller than an outer shape of the distal end part body 34. A width (a length in the X direction) of the two side surface portions 122b of the balloon 120 before being mounted on the distal end part body 34 is smaller than a distance between the two standing wall portions 91 in the width direction. As a result, in a case of being inserted into the distal end part body 34 from the opening portion 122a of the inner part 122, the two side surface portions 122b of the inner part 122 expand in the X direction, and the side surface portions 122b are in close contact with and fixed to the standing wall portions 91 by contractile force to return. The two side surface portions 122b of the inner part 122 function as a fixing portion that is in close contact with and fixed to the distal end part body 34.

The two protrusion portions 122j provided on the second side surface portions 122g that configure the side surface portions 122b of the inner part 122 are fitted into the groove portions 92 of the distal end part body 34 described above in a case where the balloon 120 is mounted on the distal end part body 34. The two protrusion portions 122j that are fitted into the groove portions 92 of the distal end part body 34 are provided in the side surface portions 122b that function as the fixing portion. In a case where the groove portions 92 are provided in the standing wall portions 91, the two protrusion portions 122j are provided in the first side surface portions 122f that configure the side surface portion 122b.

The inside of the inner part 122 is formed in a similar shape to the distal end part body 34 and in a shape smaller than the outer shape of the distal end part body 34, whereby the inner part 122 can be in contact and fixed from the oscillator surface 51 and the surface on the opposite side to the oscillator surface 51. As a result, the inner part 122 can also be in close contact with and fixed to the oscillator surface 51 and to the surface on the opposite side to the oscillator surface 51 of the distal end part body 34, and the balloon 120 can be firmly fixed to the distal end part body 34. The inclined surface portion 122d and the bottom surface portion 122e of the inner part 122 function as a fixing portion that is in close contact with and fixed to the distal end part body 34.

It is preferable that the balloon body 121 has a shape following the outer shape of the oscillator surface of the ultrasound transducer 50 described above. With the balloon body 121 having such a configuration, it is possible to stabilize an orientation in a case where the balloon 120 is mounted on the distal end part body 34.

FIG. 8 is a sectional view of the balloon 120. 800A is a sectional view of the balloon 120 taken along the YZ plane, and 800B is a sectional view of the balloon 120 taken along the XY plane. As shown in FIG. 8, the outer part 124 covers the inner part 122, and the outer part 124 and the inner part 122 are bonded, whereby the balloon body 121 is configured.

As shown in 800A, the inner part 122 and the outer part 124 are bonded, and a closed space can be formed between the inner part 122 and the outer part 124. This space is a storage portion 121a that stores an ultrasonic wave transmission medium. The ultrasonic wave transmission medium is stored in the storage portion 121a, whereby an oscillator surface region 124f that configures the inclined surface portion 124d of the outer part 124 can be swollen. The oscillator surface region 124f functions as a swelling portion. The oscillator surface region 124f is a region facing the oscillator surface 51 of the ultrasound transducer 50.

As described above, since the storage portion 121a of the balloon 120 is configured with the closed space between the inner part 122 and the outer part 124, it is possible to secure fluid-tightness in the balloon 120 itself. Accordingly, unlike the related art in which fluid-tightness is secured between the distal end part body and the balloon, it is not essential that the balloon 120 has an annular groove shape in locking the distal end part body and the balloon. With the balloon 120, it is possible to avoid an increase in diameter and an increase in size of the distal end part body 34 due to the annular groove shape. The balloon 120 gives a degree of freedom for design to the shape of the distal end part body 34. As shown in FIG. 7, the opening portion 122a of the balloon 120 can have a rectangular shape, instead of an annular shape.

It is preferable that the inner part 122 and the outer part 124 are not in close contact, and that a clearance is provided therebetween. The inner part 122 and the outer part 124 are not in close contact, whereby it is possible to prevent it from being difficult for the ultrasonic wave transmission medium to be supplied in a case of supplying the ultrasonic wave transmission medium to the storage portion 121a since an outer surface of the inner part 122 and an inner surface of the outer part 124 stick to each other. As described below, in a case of adhering and assembling the inner part 122 and the outer part 124, it can be made difficult for the inner part 122 and the outer part 124 to stick to each other. The clearance means a state in which the outer surface of the inner part 122 and the inner surface of the outer part 124 are separated from each other by a given distance.

As shown in 800A, in a region surrounded by a quadrangle, the inner part 122 and the outer part 124 are bonded by an adhesive or the like. A clearance is not present in an adhesion portion 121b of the inner part 122 and of the outer part 124 bonded by the adhesive. The clearance may not be provided in the entire region between the inner part 122 and the outer part 124.

The adhesion portion 121b may be, for example, at a position corresponding to the top surface portion 122c (not shown) of the inner part 122 and to the top surface portion 124c (not shown) of the outer part 124.

The adhesion portion 121b does not expand even though the ultrasonic wave transmission medium is supplied into the balloon 120. Thus, even though the puncture needle 100 is led out from the outlet port 52, the proximal end side (Z(−) side) of the balloon 120 does not expand. Therefore, it is possible to restrain the puncture needle 100 led out from the outlet port 52 from being brought into contact with the swollen balloon 120. The adhesion portion 121b functions as a swelling restricting part capable of suppressing swelling except in the oscillator surface region 124f described below. The adhesion portion 121b suppresses swelling of a proximal end side (Z(−) side) of the oscillator surface region 124f.

The inclined surface portion 124d of the outer part 124 includes the oscillator surface region 124f and a thick portion 124g. The thick portion 124g is disposed on the other end side (Z(+) side) opposite to one end side (Z(−) side) in the first direction (Z direction) and is formed to have a thickness greater than a thickness of the oscillator surface region 124f. The thick portion 124g suppresses swelling of a distal end side (Z(+) side) of the oscillator surface region 124f of the outer part 124 in a case where the ultrasonic wave transmission medium is supplied to the storage portion 121a. The thick portion 124g functions as a swelling restricting part and can make the oscillator surface region 124f more effectively swollen.

Since the oscillator surface region 124f is formed to have a film thickness thinner than other regions of the outer part 124 including the thick portion 124g, the oscillator surface region 124f can be easily swollen compared to other regions.

The bottom surface portion 122e of the inner part 122 that functions as a fixing portion of the balloon 120 has the locking portion 122k inside. The locking portion 122k is configured with a plane substantially parallel to the XY plane and stands in the Y(+) direction as viewed from the distal end side (Z(+) side). The locking portion 122k is locked to the stepped portion 94 of the distal end part body 34 described above in a case where the balloon 120 is mounted on the distal end part body 34.

The inner part 122 of the balloon body 121 has a communication path 122m that communicates with the storage portion 121a, in the bottom surface portion 122e on an opposite side to the oscillator surface region 124f. The communication path 122m has an opening in the Z(−) direction, and the storage portion 121a communicates with the outside through the communication path 122m.

A tube 140 is inserted into the communication path 122m of the bottom surface portion 122e of the inner part 122 that functions as a fixing portion of the balloon 120, whereby it is possible to attach the tube 140 to the balloon 120. The attachment of the tube 140 to the balloon 120 may be attachable and detachable or may be inseparable. The tube 140 is a tubular member that has a space to be a flow channel inside. The ultrasonic wave transmission medium can be supplied from the flow channel of the tube 140 to the storage portion 121a in the balloon 120 through the communication path 122m. As a result, it is possible to expand the oscillator surface region 124f that configures the outer part 124 of the balloon 120. The tube 140 is attached to the balloon 120, whereby a supply pipe line for supplying the ultrasonic wave transmission medium to the balloon 120 does not need to be provided in the insertion part 12 of the endoscope 1. Thus, it is possible to achieve a reduction in diameter of the insertion part 12. The balloon 120 (and the tube 140) is disposable, whereby there is no need to perform cleaning and sterilization of the tube 140. In recent years, a minimum pipe line diameter to be sterilized by a sterilization device has been defined, and there has been an increasing demand for cleaning, disinfection, and sterilization. By making the tube 140 disposable, it is possible to omit work of cleaning and sterilization of a supply pipe line.

The tube 140 is configured to more difficultly expand than the balloon body 121 (inner part 122 and outer part 124). That is, the balloon body 121 is configured to more easily expand than the tube 140. A configuration in which the balloon body 121 more easily expands than the tube 140 can be realized, for example, by making a film thickness of the balloon body smaller than a film thickness of the tube or by using a material having an expansion coefficient greater than the material for the tube 140, as the material for the balloon body 121.

As shown in 800B, the outer part 124 has the side surface portions 124b (that is, thick portions) that are formed to have a thickness greater than the thickness of the oscillator surface region 124f, on both sides in the second direction (X direction) perpendicular to the first direction (Z direction) of the oscillator surface region 124f. The outer part 124 has transition portions 124h that connect the oscillator surface region 124f and the side surface portions 122b. The transition portions 124h increase in thickness from the oscillator surface region 124f toward the side surface portions 124b. The transition portions 124h can suppress swelling of the oscillator surface region 124f in the X direction in a case where the ultrasonic wave transmission medium is supplied to the storage portion 121a, and function as a swelling restricting part. The transition portions 124h can be configured with a part on the Y(+) side of the side surface portions 124b.

As shown in 800B, in the balloon body 121, the side surface portions 122b of the inner part 122 and the side surface portions 124b of the outer part 124 are disposed to face each other on both sides in the second direction (X direction) perpendicular to the first direction (Z(+) direction) of the oscillator surface region 124f. The balloon body 121 has adhesion regions 121c where the inner part 122 and the outer part 124 are adhered by an adhesive or the like, between the side surface portions 122b and the side surface portion 124b facing each other. The adhesion regions 121c suppress swelling of the oscillator surface region 124f in the X direction in a case where the ultrasonic wave transmission medium is supplied to the storage portion 121a, and function as a swelling restricting part. The adhesion regions 121c may be partial regions between the side surface portions 122b and the side surface portion 124b as shown in 800B or may be the entire regions between the side surface portions 122b and the side surface portion 124b facing each other.

As shown in 800B, the bottom surface portion 124e of the outer part 124 has a recess portion 124i that has a semi-spherical shape a in sectional view and that extends in the Z direction, at substantially a center in the width direction (X direction). The recess portion 124i is a portion that configures a part of the clearance and that communicates with the communication path 122m of the inner part 122. It is possible to easily supply the ultrasonic wave transmission medium to the storage portion 121a with the recess portion 124i.

FIG. 9 is a sectional view of the balloon 120 illustrating a flow of the ultrasonic wave transmission medium supplied to the balloon 120. 900A is a sectional view of the balloon 120 taken along the YZ plane, and 900B is a sectional view of the balloon 120 taken along the XY plane.

A flow channel through which the ultrasonic wave transmission medium is supplied to the storage portion 121a will be described with reference to FIG. 9. As shown in 900A, the tube 140 is attached to the communication path 122m of the outer part 124 for supplying the ultrasonic wave transmission medium to the storage portion 121a. Since the tube 140 is disposed on an opposite side (Y(−) side) to the oscillator surface region 124f, swelling of the oscillator surface region 124f is not obstructed. The acquisition of the observation image with the observation optical system 40 is not obstructed.

The ultrasonic wave transmission medium is supplied to the balloon 120 through the tube 140. The ultrasonic wave transmission medium is supplied to a region having the clearance between the inner part 122 and the outer part 124 through the communication path 122m of the inner part 122. A region between the bottom surface portion 122e of the inner part 122 and the bottom surface portion 124e of the outer part 124 is filled with the ultrasonic wave transmission medium, and a region between the inclined surface portion 122d of the inner part 122 and the inclined surface portion 124d of the outer part 124 is filled with the ultrasonic wave transmission medium. The ultrasonic wave transmission medium is finally stored in the storage portion 121a that is mainly configured with the oscillator surface region 124f and the inclined surface portion 122d.

As shown in 900B, a region between the bottom surface portion 122e of the inner part 122 and the bottom surface portion 124e of the outer part 124 is filled with the ultrasonic wave transmission medium, and a region between the side surface portion 122b of the inner part 122 and the side surface portion 124b of the outer part 124 is filled with the ultrasonic wave transmission medium. The ultrasonic wave transmission medium is finally stored in the storage portion 121a that is mainly configured with the oscillator surface region 124f and the inclined surface portion 122d.

FIG. 10 is a sectional view showing a state in which the oscillator surface region of the balloon for an ultrasonic endoscope is swollen, and is a sectional view of the balloon 120 taken along the YZ plane. As shown in FIG. 10, in a case where the ultrasonic wave transmission medium is stored in the storage portion 121a, the oscillator surface region 124f is most swollen.

As described above, the oscillator surface region 124f has a film thickness thinner than other regions of the outer part 124 including the thick portion 124g. As a result, the oscillator surface region 124f is more easily swollen than other regions.

In regions other than the oscillator surface region 124f, for example, the thick portion 124g, the adhesion portion 121b, the transition portions 124h (not shown), and the adhesion regions 121c (not shown) that function as a swelling restricting part are provided. With the thick portion 124g and the adhesion portion 121b, swelling of regions (regions in the Z(+) direction and the Z(−) direction with respect to the oscillator surface region 124f) other than the oscillator surface region 124f is suppressed. With the transition portions 124h and the adhesion regions 121c, swelling of regions (regions in the X direction with respect to the oscillator surface region 124f) other than the oscillator surface region 124f is suppressed.

In the balloon 120, the oscillator surface region 124f is made most swollen, whereby it is possible to suppress swelling of a bottom surface side and side surface sides of the balloon 120, and to insert the distal end part body 34 to a periphery in a case of inserting the distal end part body 34 with the balloon 120 mounted thereon into the body cavity.

The tube 140 is a member that does not expand compared to the balloon 120. Accordingly, in a case where the ultrasonic wave transmission medium is supplied to the balloon 120 through the tube 140, since expansion of the tube 140 is suppressed, it is possible to effectively supply the ultrasonic wave transmission medium to the balloon 120.

Figure 11:
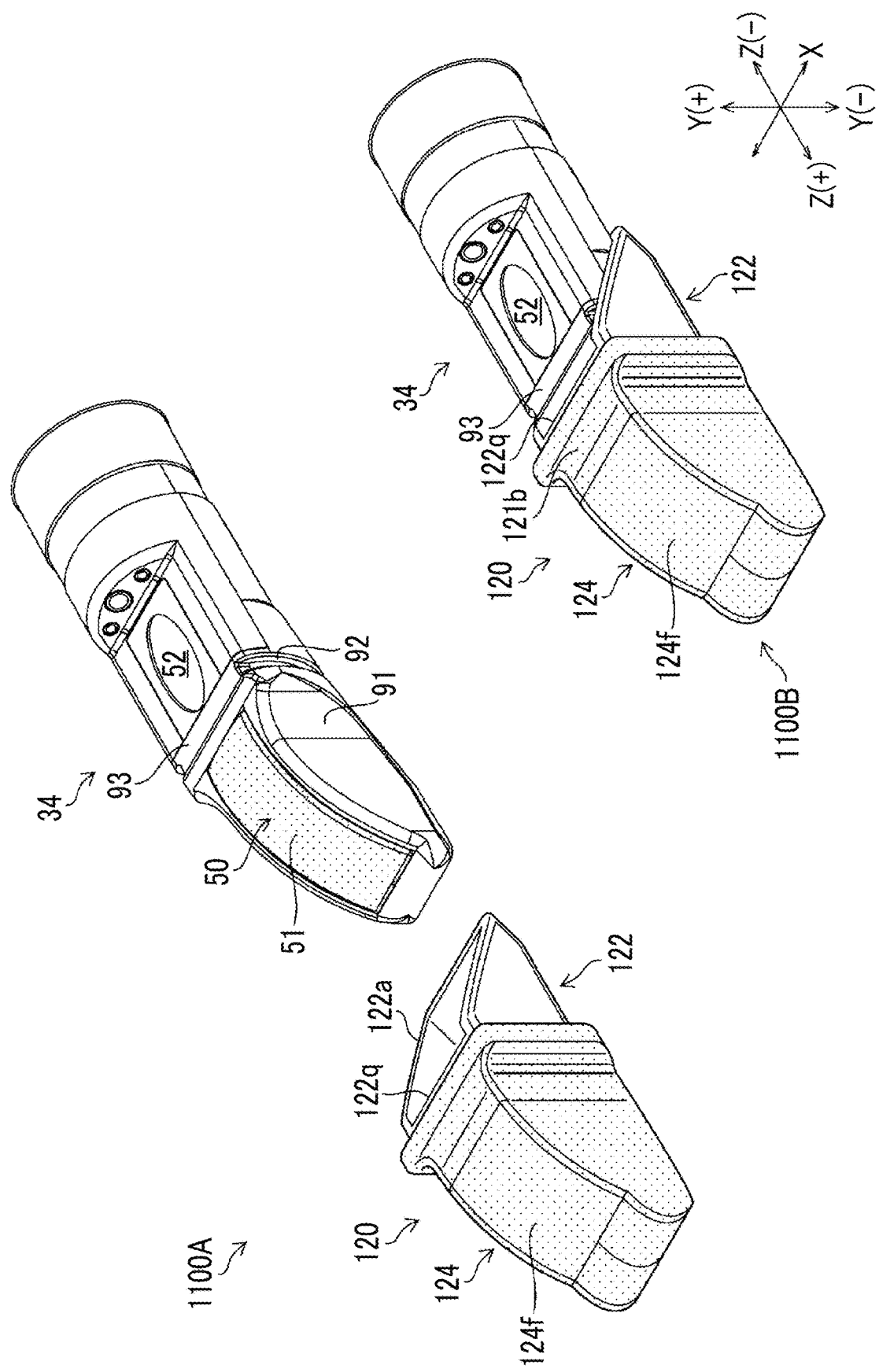
FIG. 11 is a perspective view illustrating mounting of the balloon for an ultrasonic endoscope with the tube omitted, on the distal end part body.

Next, mounting of the balloon 120 on the distal end part body 34 will be described. FIG. 11 is a perspective view illustrating mounting of the balloon 120 with the tube omitted, on the distal end part body 34. 1100A shows a state before the balloon 120 is mounted on the distal end part body 34. The opening portion 122*a* of the balloon 120 and the distal end side of the distal end part body 34 are aligned. 1100B shows a state after the balloon 120 is mounted on the distal end part body 34. The opening portion 122*a* of the balloon 120 is attached to the distal end part body 34, and the balloon 120 is mounted on the distal end part body 34. The inner part 122 covers the ultrasound transducer 50 of the ultrasonic attachment part 34*a* and further covers a part of the outer peripheral surface of the outlet port forming portion 34*b* other than the opening forming surface 71. The outer part 124 is disposed at a position covering the ultrasound transducer 50 of the ultrasonic attachment part 34*a*.

As described above, at least the side surface portions 122*b* are in close contact with and fixed to the standing wall portions 91 by contractile force of the side surface portion 122*b* (not shown) as a fixing portion of the inner part 122.

A flat portion 122*q* of the inner part 122 that functions as a fixing portion is provided on the proximal end side of the oscillator surface region 124*f* of the balloon 120 that functions as a swelling portion. The plane portion 93 between the ultrasound transducer 50 and the outlet port 52 is in close contact with and fixed to the flat portion 122*q* of the balloon 120. The flat portion 122*q* is provided, whereby it is possible to extend a distance between the oscillator surface region 124*f* and the outlet port 52. Therefore, it is possible to restrain the puncture needle 100 led out from the outlet port 52 from being brought into contact with the swollen balloon 120. The flat portion 122*q* may be at a position of the adhesion portion 121*b* described above.

Since the balloon 120 has a shape in which the ultrasound transducer 50 is offset, as a whole, it is possible to allow a worker to easily recognize an orientation in which the balloon 120 is mounted on the distal end part body 34.

With the balloon 120 of the present embodiment, the inner part 122 and the outer part 124 are bonded to form a sealed space, and the sealed space is used as the storage portion 121*a* that stores the ultrasonic wave transmission medium. Accordingly, the outer shape of the distal end part body 34 is not limited to a shape for securing fluid-tightness and can be designed in consideration of a reduction in diameter of the distal end part body 34 and a lead-out route of the puncture needle 100.

In a case where the tube 140 is attached to the balloon 120 and the ultrasonic wave transmission medium is supplied to the storage portion 121*a* through the tube 140, as shown in FIG. 11, there is no need to provide a supply pipe line in the distal end part body 34 of the endoscope 1.

Figure 12:
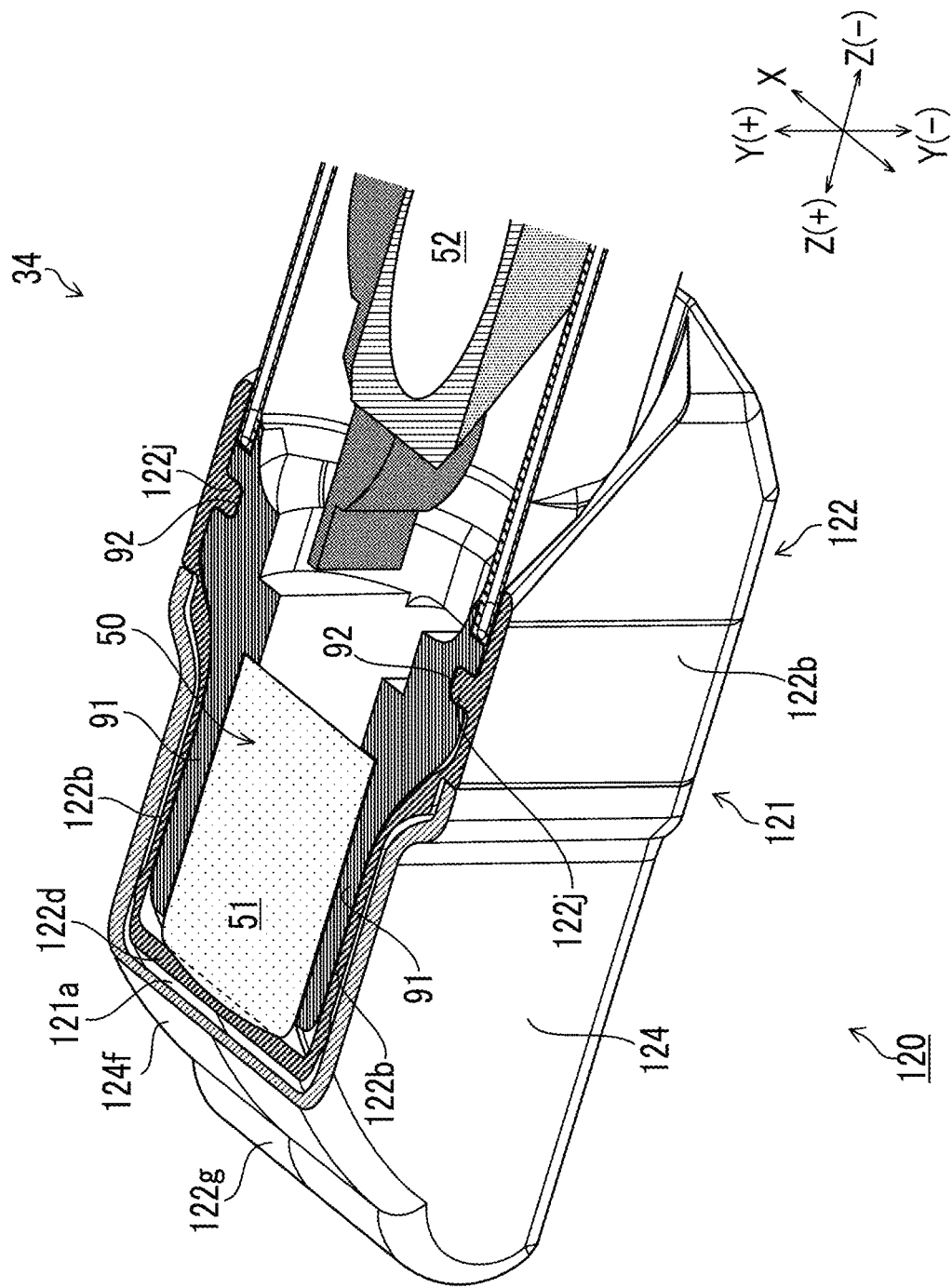
FIG. 12 is a perspective view of a distal end part body on which the balloon for an ultrasonic endoscope with the tube omitted is mounted, taken along an XZ plane.

FIG. 12 is a diagram of the distal end part body 34 on which the balloon 120 with the tube omitted is mounted, taken along the XZ plane. As shown in FIG. 12, the side surface portion 122*b* as a fixing portion of the inner part 122 that configures the balloon 120 has the protrusion portions 122*j*. The groove portions 92 are provided between the ultrasound transducer 50 and the outlet port 52. The protrusion portions 122*j* and the groove portions 92 are fitted. The groove portions 92 and the protrusion portions 122*j* are fitted, whereby movement in a direction in which the balloon 120 and the distal end part body 34 are separated from each other is regulated, and it can be made difficult for the balloon 120 to fall off from the distal end part body 34.

In a case where the standing wall portions 91 have groove portions (not shown), protrusion portions (not shown) are provided in the side surface portions 122*b* of the balloon 120 facing the ultrasound transducer 50. The protrusion portions and the groove portions are fitted, whereby it can be made difficult for the balloon 120 to fall off from the distal end part body 34.

The balloon 120 has the storage portion 121*a* between the oscillator surface region 124*f* facing the oscillator surface 51 and the inclined surface portion 122*d*.

Figure 13:
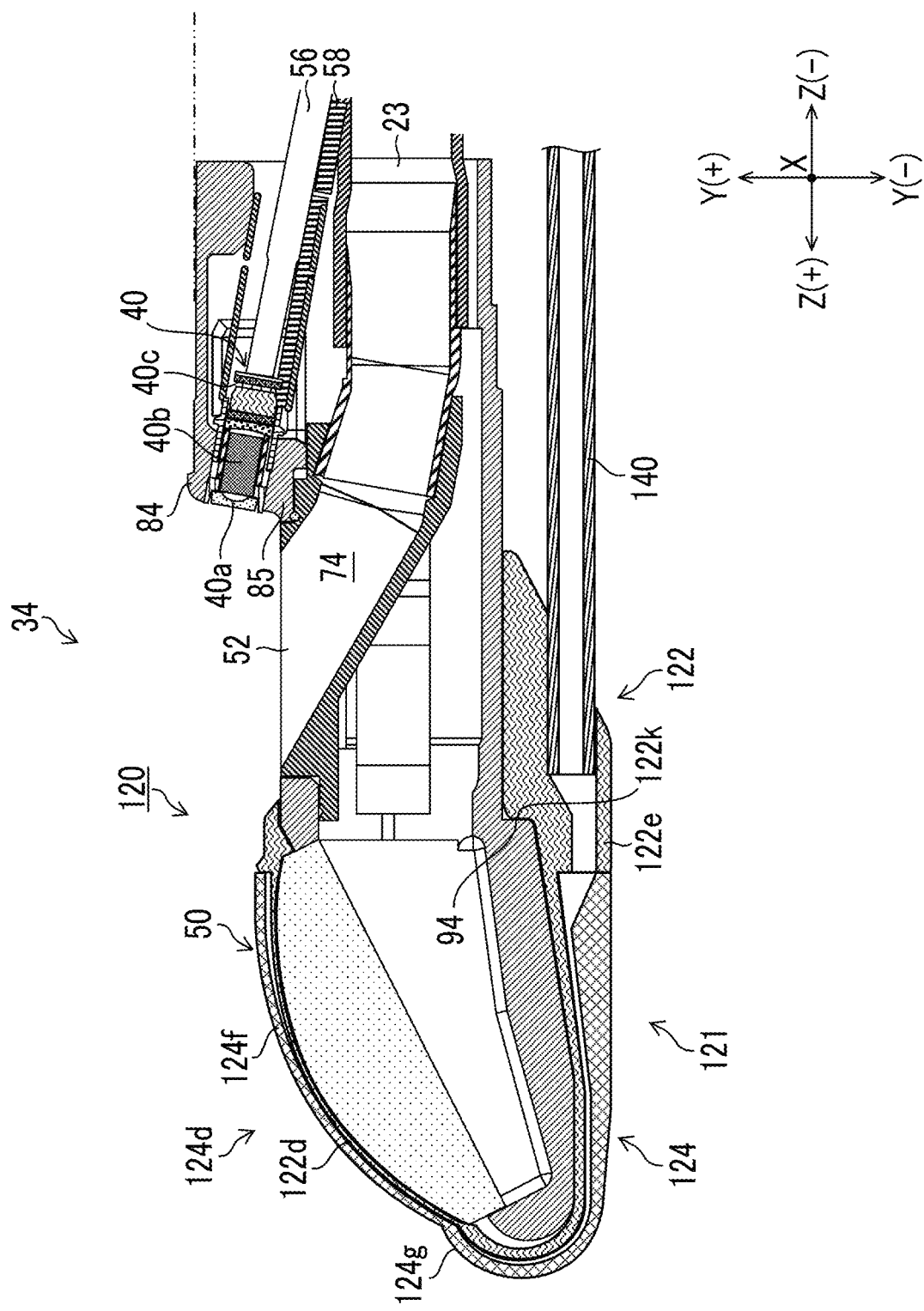
FIG. 13 is a sectional view of the distal end part body on which the balloon for an ultrasonic endoscope is mounted, taken along a YZ plane.

FIG. 13 shows a cross section of the distal end part body 34 on which the balloon 120 is mounted, taken along the YZ plane. As shown in FIG. 13, the distal end part body 34 has the stepped portion 94 in a surface on the opposite side to the oscillator surface 51 on the proximal end side (Z(−) direction side) of the ultrasound transducer 50. The bottom surface portion 122*e* as a fixing portion of the inner part 122 that configures the balloon 120 has the locking portion 122*k*. The stepped portion 94 and the locking portion 122*k* are locked, whereby it is possible to restrain the balloon 120 from falling off from the distal end part body 34. It is possible to restrain falling off of the balloon 120 in a case where the insertion part 12 of the endoscope 1 on which the balloon 120 is mounted is pulled out from the body cavity in the Z(−) direction. The tube 140 is attached in parallel with the insertion part 12 and is connected to a supply and exhaust unit of the ultrasonic wave transmission medium, such as a syringe, near the operating part 10.

FIG. 14 is a perspective view of the balloon 120 with the tube omitted as viewed from the Z(−) direction to the Z(+) direction. The bottom surface portion 122*e* of the inner part 122 has a tapered portion 122*n* on the proximal end side (Z(−) side). The tapered portion 122*n* is inclined in the Y(+) direction while extending in the Z(−) direction. The two side surface portions 122*b* of the inner part 122 have tapered portions 122*p* on the proximal end side (Z(−) side), respectively. The two tapered portions 122*p* are inclined in an orientation approaching each other while extending in the Z(−) direction.

The tapered portions 122*n* are provided, whereby force in the first direction (Z direction) can be released in the Y direction. The tapered portion 122*p* is provided, whereby force in the first direction (Z direction) can be released in the X direction. As a result, in a case where the distal end part is inserted into and pulled out from the body cavity, force applied due to contact with a tissue in the body can be released in the Y direction and in the X direction. Therefore, it is possible to restrain the balloon 120 from falling off from the distal end part body 34.

Although a case where the balloon 120 has the tapered portions 122*n* and the tapered portion 122*p* has been described, any one of the tapered portions 122*n* or the tapered portion 122*p* may be provided.

The balloon 120 of the embodiment can make the oscillator surface region 124*f* of the outer part 124 facing the oscillator surface 51 of the ultrasound transducer 50 most swollen by restricting a part of the balloon body 121 with the swelling restricting part in a case where the ultrasonic wave transmission medium is stored inside the storage portion 121*a* of the balloon body 121. As a result, in a case where the balloon 120 is swollen, it is possible to achieve a reduction in outer diameter of the balloon 120, and since the balloon 120 is not swollen on an opposite side of the oscillator surface 51, it is possible to stably bring the oscillator surface 51 into contact with a site to be observed in a body cavity through the balloon 120.

In the above-described embodiment, although an example where the balloon 120 has the balloon body 121 having the two-layer structure composed of the inner part 122 and the outer part 124 has been described, the present invention is not limited to the balloon body 121 having the two-layer structure. For example, in addition to the inner part 122 and the outer part 124, a separate member may be laminated to form a balloon body having a structure of three layers or more.

Figure 15:
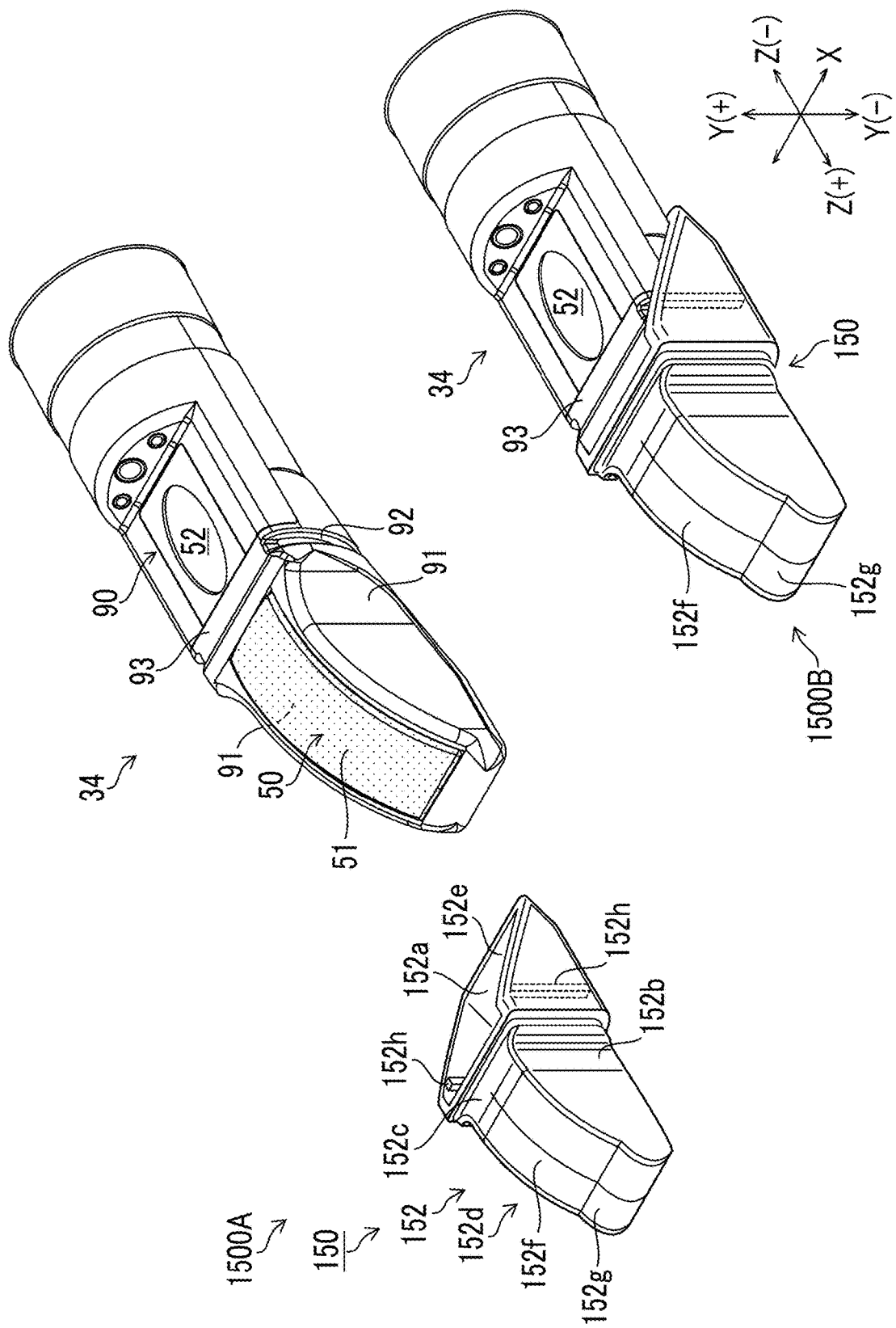
FIG. 15 is a perspective view illustrating mounting of a balloon for an ultrasonic endoscope with a tube omitted of another embodiment on the distal end part body.

Next, a balloon of another embodiment will be described. FIG. 15 is a perspective view illustrating mounting of a balloon 150 of another embodiment on the distal end part body 34. The Z direction in the drawing corresponds to a first direction of the present invention and corresponds to a longitudinal direction of the insertion part.

1500A shows a state before the balloon 150 is mounted on the distal end part body 34. 1500B shows a state after the balloon 150 is mounted on the distal end part body 34. Unlike the balloon 120, the balloon 150 is a balloon that is configured with one layer.

The structure of the balloon 150 will be described. The balloon 150 comprises a balloon body 152, has an opening portion 152a at one end in the first direction (Z direction), and comprises two side surface portions 152b disposed to face each other, a top surface portion 152c, an inclined surface portion 152d, and a bottom surface portion 152e. The balloon body 152 is configured in a bottomed tubular shape having the opening portion 152a to be attached to the distal end part body 34, and portions other than the opening portion 152a are closed by the two side surface portions 152b, the top surface portion 152c, the inclined surface portion 152d, and the bottom surface portion 152e. Since the balloon body 152 is configured in a bottomed tubular shape, the balloon body 152 can store the ultrasonic wave transmission medium inside.

The inclined surface portion 152d has an oscillator surface region 152f facing the oscillator surface 51 of the ultrasound transducer 50. Since the oscillator surface region 152f is configured to have a film thickness thinner than other portions of the balloon body 152, the oscillator surface region 152f is configured to be more easily swollen than other regions.

Two protrusion portions 152h facing each other are provided on the proximal end side (Z(−) side) of the side surface portions 152b. The two protrusion portions 152h are in parallel in the Y direction and protrude in a direction approaching each other.

As shown in 1500A, the opening portion 152a of the balloon 150 and a distal end side of the distal end part body 34 are aligned, and as shown in 1500B, the opening portion 152a of the balloon 150 is attached to the distal end part body 34, and the balloon 150 is mounted on the distal end part body 34.

The protrusion portions 152h of the balloon 150 and the groove portions 92 of the distal end part body 34 are fitted, whereby it can be made difficult for the balloon 150 to fall off from the distal end part body 34.

The ultrasonic wave transmission medium is stored in a space configured with the balloon 150 and with the distal end part body 34, whereby the oscillator surface region 152f of the balloon body 152 is swollen.

In this case, a swelling restricting part is provided in the balloon body 152, whereby the oscillator surface region 124f can be more effectively swollen. For example, the swelling restricting part is a thick portion 152g that is disposed on the other end side (Z(+) side) opposite to one end (Z(−) side) of the inclined surface portion 152d in the first direction (Z direction). In a case where the ultrasonic wave transmission medium is supplied inside the balloon body 152, the thick portion 152g suppresses swelling of a distal end side (Z(+) side) of the oscillator surface region 152f.

As another swelling restricting part, the two side surface portions 152b are in close contact with and fixed to the standing wall portions 91. The side surface portions 152b in close contact with and fixed to the standing wall portions 91 suppress swelling of the oscillator surface region 152f in the width direction (X direction) in a case where the ultrasonic wave transmission medium is supplied inside the balloon body 152. A width (a length in the X direction) of the two side surface portions 152b of the balloon 150 before being mounted on the distal end part body 34 is made smaller than a distance (a length in the X direction) between the two standing wall portions 91 in the width direction, whereby the two side surface portions 152b can be in close contact with and fixed to the standing wall portions 91.

As another swelling restricting part, the top surface portion 152c and the plane portion 93 of the distal end part body 34 are in close contact and fixed. The top surface portion 152c in close contact with and fixed to the plane portion 93 suppresses swelling of the proximal end side (Z(−) side) of the oscillator surface region 152f in a case where the ultrasonic wave transmission medium is supplied inside the balloon body 152. A distance (a length in the Y direction) between the top surface portion 152c and the bottom surface portion 152e of the balloon 150 before being mounted on the distal end part body 34 is made smaller than a height (a length in the Y direction) of the distal end part body 34 to be portions to which the top surface portion 152c and the bottom surface portion 152e are in close contact with and fixed, whereby the top surface portion 152c can be in close contact with and fixed to the plane portion 93.

The balloon 150 of another embodiment can make the oscillator surface region 152f of the balloon body 152 facing the oscillator surface 51 of the ultrasound transducer 50 most swollen by restricting a part of the balloon body 152 with the swelling restricting part in a case where the ultrasonic wave transmission medium is stored inside the balloon body 152. As a result, in a case where the balloon 150 is swollen, it is possible to achieve a reduction in outer diameter of the balloon 150, and since the balloon 150 is not swollen on an opposite side of the oscillator surface 51, it is possible to stably bring the oscillator surface 51 into contact with a site to be observed in a body cavity through the balloon 150.

EXPLANATION OF REFERENCES

1: ultrasonic endoscope
10: operating part
12: insertion part
14: universal cord
16: angle lever
22: suction button
23: treatment tool insertion channel
24: treatment tool inlet port
30: soft part
32: bending part
34: distal end part body
34a: ultrasonic attachment part
34b: outlet port forming portion
34c: body part
38: longitudinal axis 40: observation optical system
40a: observation window
40b: lens system
40c: imaging element
44: illumination optical system
44a: illumination window
50: ultrasound transducer
51: oscillator surface
52: treatment tool outlet port
54: signal cable
56: signal cable
58: light guide
71: opening forming surface
74: pipe line
82: optical system storage portion
84: convex surface
85: stepped surface
91: standing wall portion
92: groove portion
93: plane portion
94: stepped portion
100: puncture needle
120: balloon for ultrasonic endoscope
121: balloon body
121a: storage portion
121b: adhesion portion
121c: adhesion region
122: inner part
122a: opening portion
122b: side surface portion
122c: top surface portion
122d: inclined surface portion
122e: bottom surface portion
122f: first side surface portion
122g: second side surface portion
122h: stepped portion
122i: flange portion
122j: protrusion portion
122k: locking portion
122m: communication path
122n: tapered portion
122p: tapered portion
122q: flat portion
124: outer part
124a: opening portion
124b: side surface portion
124c: top surface portion
124d: inclined surface portion
124e: bottom surface portion
124f: oscillator surface region
124g: thick portion
124h: transition portion
124i: recess portion
140: tube
150: balloon
152: balloon body
152a: opening portion
152b: side surface portion
152c: top surface portion
152d: inclined surface portion
152e: bottom surface portion
152f: oscillator surface region
152g: thick portion
152h: protrusion portion

What is claimed is:

1. A balloon for an ultrasonic endoscope that is mounted to cover an outside surface of an ultrasound transducer provided in a distal end part body on a distal end side of an insertion part, the balloon comprising:
 a bottomed tubular balloon body that has an opening portion provided at one end in a first direction corresponding to a longitudinal direction of the insertion part and attached to the distal end part body, covers an oscillator surface of the ultrasound transducer, and stores an ultrasonic wave transmission medium inside, to be swellable; and
 a swelling restricting part that, in a case where the ultrasonic wave transmission medium is stored inside the balloon body, makes an oscillator surface region facing the oscillator surface of the ultrasound transducer most swollen by restricting a part of the balloon body,
 wherein the balloon body has at least a two-layer structure including an inner part that has the opening portion at one end and an outer part that covers the inner part and that is bonded on an opening portion side,
 wherein the outer part includes thick portions that are formed to have a thickness greater than a thickness of the oscillator surface region, on both sides of the oscillator surface region in a second direction perpendicular to the first direction, and transition portions that are formed between the thick portions and the oscillator surface region, and the swelling restricting part comprises the transition portions.

2. The balloon for an ultrasonic endoscope according to claim 1,
 wherein a storage portion that stores the ultrasonic wave transmission medium is provided between the inner part and the outer part, and
 the outer part has the oscillator surface region.

3. The balloon for an ultrasonic endoscope according to claim 2,
 wherein an adhesion portion for bonding the inner part and the outer part is provided, and the swelling restricting part comprises the adhesion portion.

4. The balloon for an ultrasonic endoscope according to claim 2,
 wherein the outer part includes a thick portion that is formed to have a thickness greater than a thickness of the oscillator surface region, on the other end side opposite to the one end in the first direction, and the swelling restricting part comprises the thick portion.

5. The balloon for an ultrasonic endoscope according to claim 2,
 wherein adhesion regions of the inner part and of the outer part are provided on both sides of the oscillator surface region in the second direction perpendicular to the first direction, and the swelling restricting part comprises the adhesion regions.

6. The balloon for an ultrasonic endoscope according to claim 1,
 wherein the balloon body has a region smaller than a distance between standing wall portions provided on both sides of the ultrasound transducer before mounting on the distal end part body.

7. The balloon for an ultrasonic endoscope according to claim 1,
 wherein the balloon body includes a protrusion portion that protrudes to a distal end part body side and that is fitted into a groove portion of the distal end part body formed on a proximal end side of the ultrasound transducer.

8. The balloon for an ultrasonic endoscope according to claim 1, wherein the balloon body includes a locking portion that is locked to a stepped portion formed on a surface of the distal end part body on an opposite side of the ultrasound transducer.

* * * * *